(12) United States Patent
Mehta et al.

(10) Patent No.: US 11,465,972 B2
(45) Date of Patent: Oct. 11, 2022

(54) INHIBITORS OF OXIDIZED LOW-DENSITY LIPOPROTEIN RECEPTOR 1 AND METHODS OF USE THEREOF

(71) Applicants: United States Government as represented by the Department of Veterans Affairs, Washington, DC (US); Bioventures, LLC, Little Rock, AR (US)

(72) Inventors: Jawahar L. Mehta, Little Rock, AR (US); Magomed Khaidakov, Little Rock, AR (US); Kottayil I. Varughese, Little Rock, AR (US); Shraddha Thakkar, Little Rock, AR (US); Yao Dai, Little Rock, TN (US); Peter Crooks, Little Rock, AR (US); Narsimha Reddy Penthala, Little Rock, AR (US)

(73) Assignees: THE UNITED STATES GOVERNMENT AS REPRESENTED BY THE DEPARTMENT OF VETERANS AFFAIRS, Washington, DC (US); BIOVENTURES, LLC, Little Rock, AR (US)

( * ) Notice: Subject to any disclaimer, the term of this patent is extended or adjusted under 35 U.S.C. 154(b) by 0 days.

(21) Appl. No.: 16/721,103

(22) Filed: Dec. 19, 2019

(65) Prior Publication Data

US 2020/0123112 A1 Apr. 23, 2020

Related U.S. Application Data

(63) Continuation of application No. 15/771,085, filed as application No. PCT/US2016/059415 on Oct. 28, 2016, now abandoned.

(60) Provisional application No. 62/248,586, filed on Oct. 30, 2015.

(51) Int. Cl.
| | |
|---|---|
| *A61K 31/4164* | (2006.01) |
| *A61K 31/415* | (2006.01) |
| *C07D 231/12* | (2006.01) |
| *C07D 231/38* | (2006.01) |
| *C07D 231/14* | (2006.01) |
| *C07D 233/28* | (2006.01) |
| *C07D 233/22* | (2006.01) |

(52) U.S. Cl.
CPC .......... *C07D 231/12* (2013.01); *A61K 31/415* (2013.01); *A61K 31/4164* (2013.01); *C07D 231/14* (2013.01); *C07D 231/38* (2013.01); *C07D 233/22* (2013.01); *C07D 233/28* (2013.01)

(58) Field of Classification Search
CPC .......... A61K 31/415; A61K 31/4164
See application file for complete search history.

(56) References Cited

U.S. PATENT DOCUMENTS

2010/0279997 A1   11/2010   Barbier et al.
2011/0319459 A1*  12/2011   Gupta ............ A61P 25/00
                                          514/397

FOREIGN PATENT DOCUMENTS

| EP | 0485890 | * 11/1991 | ............ A61K 31/41 |
| WO | WO 2010/090875 | 8/2010 | |
| WO | WO 2013/192125 | * 12/2013 | ............ A61K 31/50 |
| WO | WO 2014/152444 | 9/2014 | |
| WO | WO 2017/075418 A1 | 5/2017 | |

OTHER PUBLICATIONS

Kiselov et al., Zhurnal Organichnoi ta Farmatsevtichnoi Khimii, vol. 7, No. 1, pp. 59-63.*
Kurihara, et al. (1967) *Annual Report of the Tohoku College of Pharmacy* 14: 65-7.
Pubchem. CID 3127806. Aug. 9, 2005. Retrieved from the Internet <URL: https://pubchem.ncbi.nlm.nih.gov/compound/3127806>.
Pubchem. CID 3144349. Aug. 9, 2005. Retrieved from the Internet <URL: https://pubchem.ncbi.nlm.nih.gov/compound/3144349>.
International Search Report and Written Opinion dated Mar. 23, 2017 by the International Searching Authority for International Application No. PCT/US2016/059415, filed on Oct. 28, 2016 and published as WO 2017/075418 on May 4, 2017 (Applicants—Bioventures, LLC & The United State of America as represented by the Department of Veteran Affairs) (16 Pages).
International Preliminary Report on Patentability dated May 1, 2018 by the International Searching Authority for International Application No. PCT/US2016/059415, filed on Oct. 28, 2016 and published as WO 2017/075418 on May 4, 2017 (Applicants—Bioventures, LLC & The United State of America as represented by the Department of Veteran Affairs) (12 Pages).
Requirement for Restriction dated Sep. 5, 2018 by the U.S. Patent and Trademark Office for U.S. Appl. No. 15/771,085, filed Apr. 30, 2018 and published as US 2018-0305318 A1 on Oct. 25, 2018 (Applicants—Bioventures, LLC & The United State of America as represented by the Department of Veteran Affairs) (7 Pages).
Response to Requirement for Restriction filed on Dec. 4, 2018 with the U.S. Patent and Trademark Office for U.S. Appl. No. 15/771,085, filed Apr. 30, 2018 and published as US 2018-0305318 A1 on Oct. 25, 2018 (Applicants—Bioventures, LLC & The United State of America as represented by the Department of Veteran Affairs) (14 Pages).
Non-final Office Action dated Mar. 22, 2019 by the U.S. Patent and Trademark Office for U.S. Appl. No. 15/771,085, filed Apr. 30, 2018 and published as US 2018-0305318 A1 on Oct. 25, 2018 (Applicants—Bioventures, LLC & The United State of America as represented by the Department of Veteran Affairs) (13 Pages).

(Continued)

*Primary Examiner* — Alicia L Otton
(74) *Attorney, Agent, or Firm* — Ballard Spahr LLP

(57) ABSTRACT

Inhibitors of oxidized low-density lipoprotein receptor 1 (LOX-1), compositions comprising inhibitors of LOX-1, and methods of using thereof are described.

11 Claims, 20 Drawing Sheets

(56) References Cited

OTHER PUBLICATIONS

Response to Office Action filed on Jun. 14, 2019 with the U.S. Patent and Trademark Office for U.S. Appl. No. 15/771,085, filed Apr. 30, 2018 and published as US 2018-0305318 A1 on Oct. 25, 2018 (Applicants—Bioventures, LLC & The United State of America as represented by the Department of Veteran Affairs) (10 Pages).
Notice of Allowance dated Sep. 19, 2019 by the U.S. Patent and Trademark Office for U.S. Appl. No. 15/771,085, filed Apr. 30, 2018 and published as US 2018-0305318 A1 on Oct. 25, 2018 (Applicants—Bioventures, LLC & The United State of America as represented by the Department of Veteran Affairs) (9 Pages).

* cited by examiner

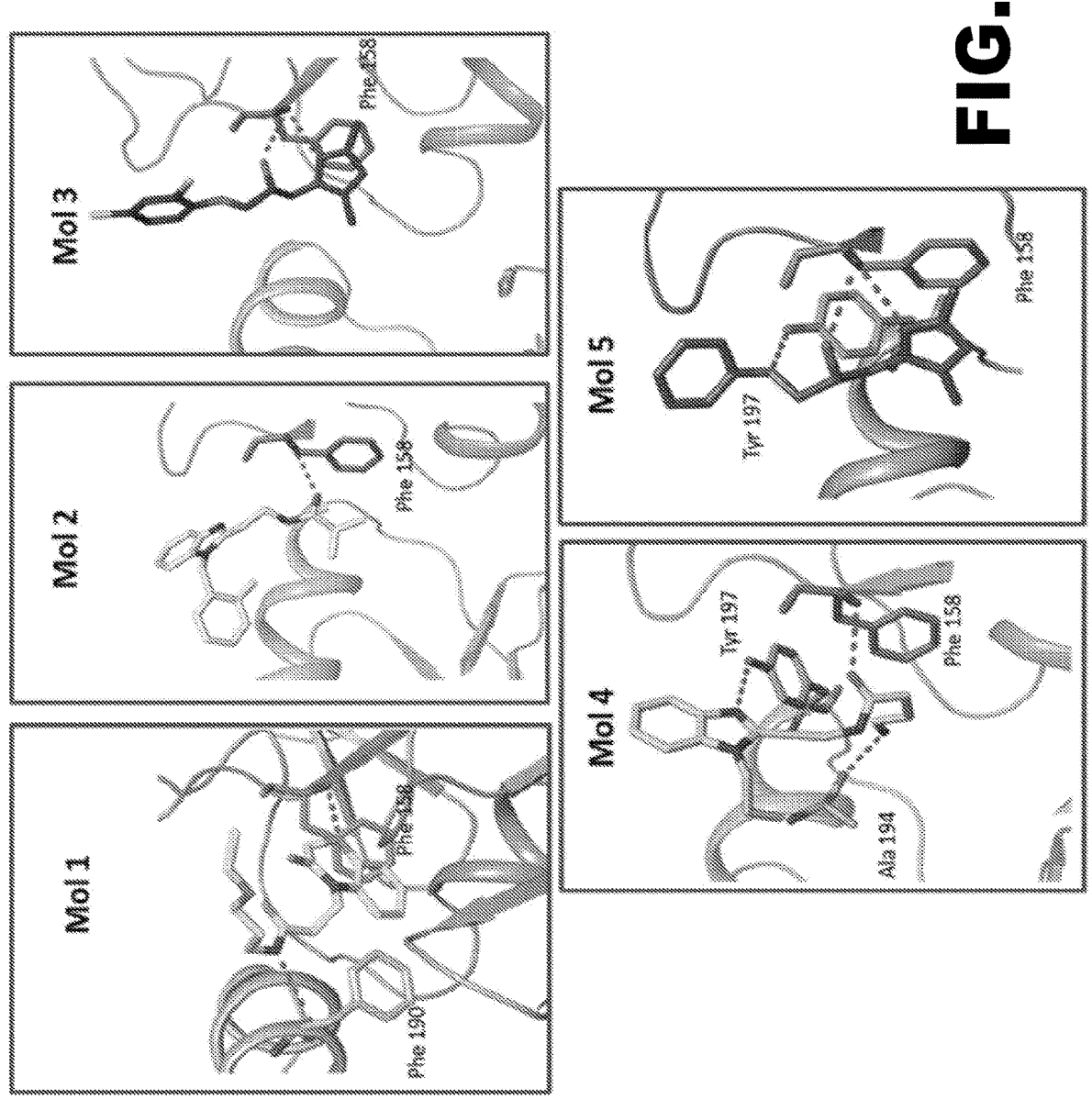

INHIBITORS OF OXIDIZED LOW-DENSITY LIPOPROTEIN RECEPTOR 1 AND METHODS OF USE THEREOF

CROSS-REFERENCE TO RELATED APPLICATIONS

This application is a continuation of U.S. application Ser. No. 15/771,085, filed on Apr. 30, 2018, which is a U.S. National Phase of International Application No. PCT/US2016/059415, filed on Oct. 28, 2016, which claims the benefit of U.S. Provisional Application No. 62/248,586, filed on Oct. 30, 2015, the contents of which are incorporated herein by reference in their entireties.

FIELD OF THE INVENTION

The disclosure describes inhibitors of oxidized low-density lipoprotein receptor 1 (LOX-1).

BACKGROUND OF THE INVENTION

Atherosclerosis continues to be a major health risk in the US and other western countries. Unfortunately, current treatments have limited effectiveness and often result in severe side effects. Additionally, no new targets for treatment have been identified in the last 15 years. Conditions leading to atherosclerosis such as diabetes, hypertension, and dyslipidemia are associated with a global increase in inflammatory signaling and generation of excessive reactive oxygen species (ROS), leading to increased production of oxidatively modified low-density lipoprotein (ox-LDL). The increased production of ox-LDL plays a central, if not obligatory, role in the atherogenic process. The lectin-like oxidized low-density lipoprotein receptor-1 (LOX-1) is expressed in endothelial cells and mediates most of the toxic effects of ox-LDL. Interaction of ox-LDL with LOX-1 activates LOX-1, and is the first key event leading to endothelial dysfunction, sub-cellular deposition of ox-LDL, recruitment of monocytes, foam cell formation, and proliferation of vascular smooth muscle cells. In addition to its role in atherosclerosis, the ox-LDL/LOX-1 interaction is also associated with several other cardiovascular conditions, including acute myocardial infarction, thrombosis, coronary restenosis, coronary heart disease, and susceptibility to diabetes. Therefore, there is a need for a LOX-1 inhibitor capable of inhibiting LOX-1 activity and LOX-1-mediated ox-LDL uptake.

SUMMARY OF THE INVENTION

In one aspect, the present disclosure provides a compound, the compound comprising Formula (I):

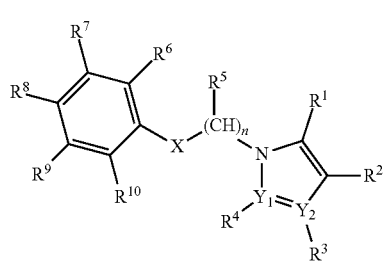

(I)

wherein:

X is selected from the group consisting of oxygen, sulfur, sulfoxide, sulfone, and nitrogen;

$Y_1$ and $Y_2$ are independently selected from the group consisting of carbon and nitrogen $R^1$, $R^2$, $R^3$, $R^4$, $R^6$, $R^7$, $R^8$, $R^9$ and $R^{10}$ are each independently selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_5$ alkyl, cyano, and halogen, with the proviso that when $Y_1$ is nitrogen, $R^4$ is absent and/or when $Y_2$ is nitrogen $R^3$ is absent;

$R^5$ independently in each occurrence is selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl, cyano, and halogen; and n is an integer from 1 to 10.

In another aspect, the present disclosure provides a compound, the compound comprising Formula (II):

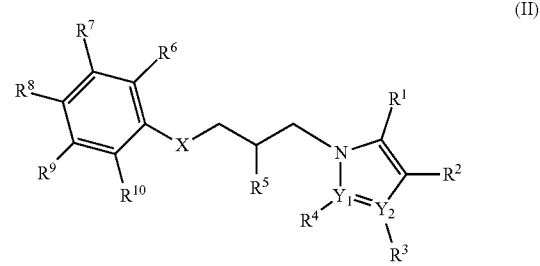

(II)

wherein:

X is selected from the group consisting of oxygen, sulfur, sulfoxide, sulfone, and nitrogen;

$Y_1$ and $Y_2$ are independently selected from the group consisting of carbon and nitrogen $R^1$, $R^2$, $R^3$, $R^4$, $R^6$, $R^7$, $R^8$, $R^9$ and $R^{10}$ are each independently selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl, and cyano, with the proviso that when $Y_1$ is nitrogen, $R^4$ is absent and/or when $Y_2$ is nitrogen $R^3$ is absent;

$R^5$ is selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl and cyano.

In still another aspect, the present disclosure provides a compound, the compound comprising Formula (XX):

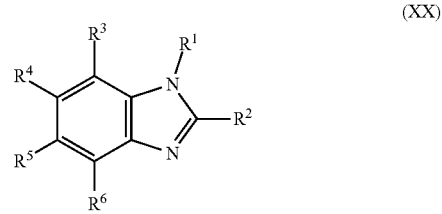

(XX)

wherein:

$R^3$, $R^4$, $R^5$ and $R^6$ are hydrogen; and $R^1$ and $R^2$ are independently selected from the group consisting of hydrocarbyl, substituted hydrocarbyl, alkyl, substituted alkyl, alkenyl, substituted alkenyl, alkynyl, substituted alkynyl, aryl, substituted aryl, aminoalkyl, substituted aminoalkyl, amidoalkyl and substituted amidoalkyl.

In still yet another aspect, the present disclosure provides a pharmaceutical composition, the composition comprising a compound of the disclosure.

In a different aspect, the present disclosure provides a method of inhibiting oxidized low-density lipoprotein receptor 1 (LOX-1), the method comprising contacting LOX-1 with a compound of the disclosure.

In another different aspect, the present disclosure provides a method of treating atherosclerosis, the method comprising administering to a subject a pharmaceutical composition comprising a compound of the disclosure.

In still another different aspect, the present disclosure provides a method of treating myocardial injury initiated during ischemic-reperfusion, the method comprising administering to a subject a pharmaceutical composition comprising a compound of the disclosure.

In still yet another different aspect, the present disclosure provides a method of treating a clinical condition resulting from metabolic syndrome, the method comprising administering to a subject a pharmaceutical composition comprising a compound of the disclosure.

In other aspects, the present disclosure provides a method of reducing buildup of atherosclerotic plaques in a subject, the method comprising administering to the subject a pharmaceutical composition comprising a compound of the disclosure.

Other features and aspects of the disclosure are described in more detail herein.

BRIEF DESCRIPTION OF THE FIGURES

The application file contains at least one photograph executed in color. Copies of this patent application publication with color photographs will be provided by the Office upon request and payment of the necessary fee.

(FIG. 1A) A cartoon showing the domain structure of LOX-1. LOX-1 is a trans-membrane protein with 273 residues comprising 4 domains. The first 36 residues form a cytoplasmic tail, followed by a single transmembrane domain (21 residues), and an extracellular region comprising two domains. The first one (58-142) is predicted to be a coil, and the second (143-273) is a C-type lectin-like domain (CTLD) responsible for ox-LDL recognition and it exists as a disulfide-linked homodimer[12,13]. (FIG. 1B) Left panel: A view of the surface representation of the C-terminal domain exhibiting the central tunnel. Right panel: A rotated view of the surface showing 'basic spine', the linear arrangement of basic residues. (FIG. 1C) A flow chart showing steps involved in virtual screening.

FIG. 2A, FIG. 2B and FIG. 2C depict the docking of the 5 lead compounds and the thermal denaturation assay: (FIG. 2A) The figure depicts the docking of the 5 lead compounds in the binding pocket of LOX-1. LOX-1 is shown as a ribbon model with one monomer in magenta and the other in blue. The compounds are shown as stick models in separate colors. (FIG. 2B) Hydrogen bonding interactions of the compounds as they dock to LOX-1. (FIG. 2C) The measured thermal shifts (in Celsius) are depicted for all five molecules. The solutions contained LOX-1 protein at 4 μM concentration. The ligand concentrations were 50 μM.

(FIG. 3A) (Upper Panel) Flow cytometry measurements using HUVECs in the presence of the five lead compounds (Mol-1-Mol-5), each a at 200 nM concentration. (Lower Panel) The percentage of internalized ox-LDL. Graphs show data as mean (±SD); n=4. *P<0.01 or <0.05 vs. control. (FIG. 3B) IC50 value for Mol-5. IC50 value (in nM) is based on inhibition of Dil-ox-LDL uptake in CHO cells overexpressing human LOX-1. Graphs show data as mean (±SD); n=5. *P<0.01 or <0.05 vs. control. (FIG. 3C) Western blotting assay showing LOX-1 protein expression in HUVECs following incubation with 200 nM Mol-1 to Mol-5 for 30 min, and subsequently exposure to 5 μg/mL ox-LDL for 6 hours. (FIG. 3D) The variation of LOX-1 mRNA expression levels at different concentrations of the compounds following exposure of HUVECs to 5 μg/mL ox-LDL. The concentrations are indicated on the X-axis and the LOX-1 mRNA levels are shown on the Y-axis. The plots for all the five molecules are shown in separate colors. Graphs show data as mean (±SD); n=3. *P<0.01 vs. control; #P<0.01 vs. ox-LDL group.

(FIG. 4A) Western blotting assay shows total ERK1/2 and phospho-ERK1/2 expression in HUVECs following exposure to 200 nM of each compound and to 5 μg/mL ox-LDL. (FIG. 4B) Western blot analyses showing phospho-p38MAPK expression in HUVECs following exposure to 200 nM of each compound for 30 min, and subsequently exposed to 5 μg/mL ox-LDL for 6 hours. (FIG. 4C) Western blotting assay shows VCAM-1 protein expression in HUVECs following incubation with 200 nM Mol-1 to Mol5 for 30 min, and subsequently exposure to 5 μg/mL ox-LDL for 6 hours. (FIG. 4D) The variation of VCAM-1 mRNA expression levels with different concentrations of the led compounds. The concentrations are indicated on the X-axis and the VCAM-1 mRNA levels are shown on the Y-axis. The plots for all five molecules are shown in separate colors. (FIG. 4E) Exposure HUVECs to 5 μg/mL ox-LDL for 6 hours could significantly increase their adhesive ability to monocytes. Mol-1, Mol-4 and Mol-5 markedly inhibited ox-LDL-induced monocyte adhesion onto the HUVECs. Graphs show data as mean (±SD); n=3 (for Western blot and PCR assays) or n=20 (for monocyte adhesion assay). *P<0.01 vs. control; #P<0.01 or <0.05 vs. ox-LDL group.

DETAILED DESCRIPTION OF THE INVENTION

Figure 1A:
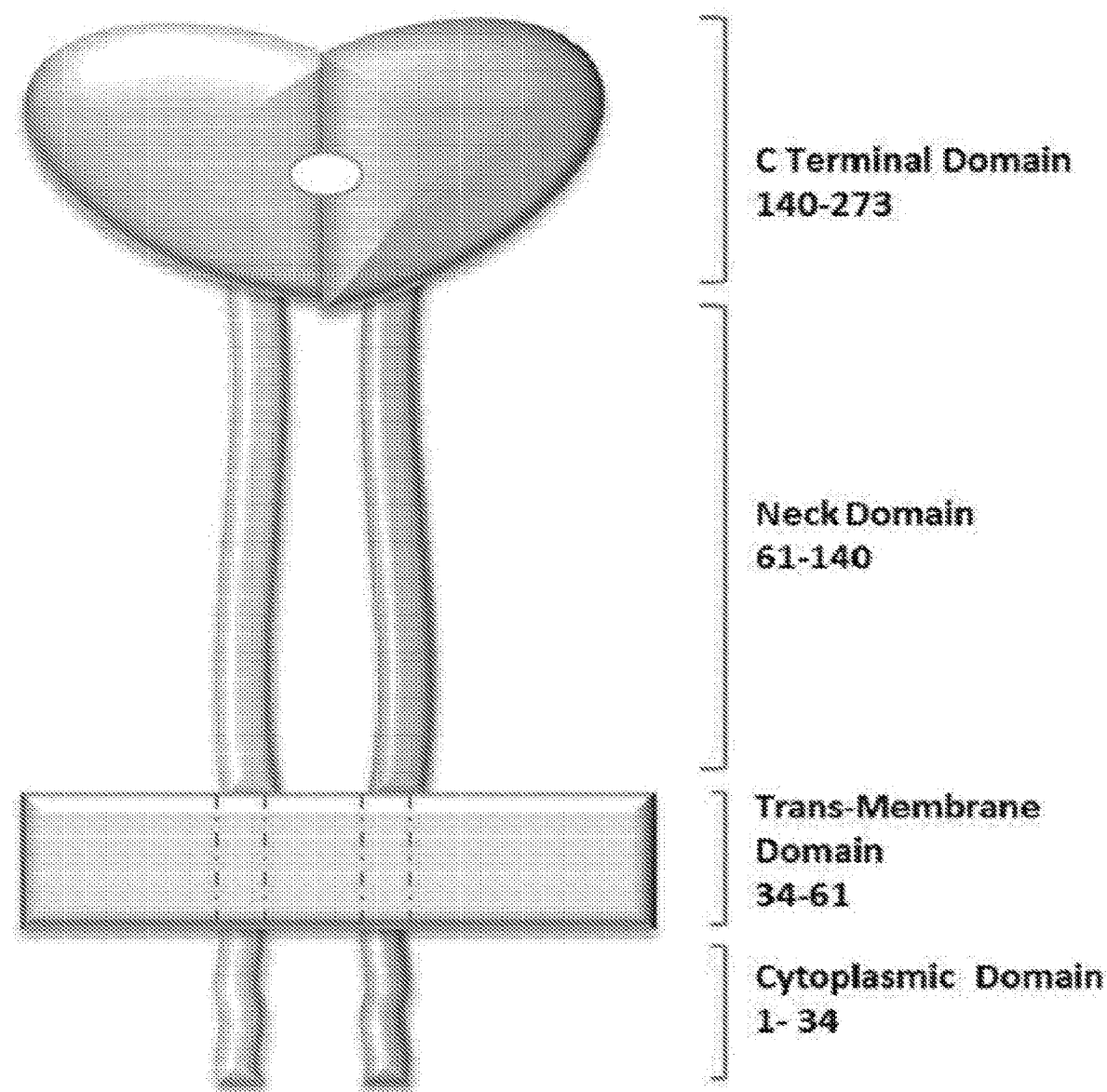
FIG. 1A, FIG. 1B and FIG. 1C depict the structure of LOX-1 and its interaction with ox-LDL.

Compounds capable of inhibiting LOX-1 activity and the interaction of ox-LDL with LOX-1 have been discovered. Compounds of the present disclosure inhibit LOX-1 activity and ox-LDL-mediated activation of LOX-1, and are useful for treating atherosclerosis without interfering with global cholesterol metabolism, and treating a number of cardiovascular diseases, such as myocardial infarction, hypertension, and heart failure. Advantageously, compounds of the disclosure may also be useful for decreasing susceptibility to diabetes.

Accordingly, the present disclosure provides compounds capable of inhibiting LOX-1 activity, a composition comprising a compound of the disclosure, and a method of using compounds capable of inhibiting LOX-1 activity to treat a condition.

I. Compounds

Compounds of the disclosure generally comprise Formula (I):

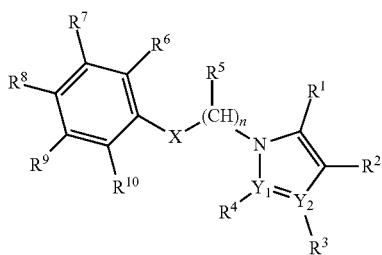

wherein:

X is selected from the group consisting of oxygen, sulfur, sulfoxide, sulfone, and nitrogen;

$Y_1$ and $Y_2$ are independently selected from the group consisting of carbon and nitrogen;

$R^1$, $R^2$, $R^3$, $R^4$, $R^6$, $R^7$, $R^8$, $R^9$ and $R^{10}$ are each independently selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl, cyano, and halogen, with the proviso that when $Y_1$ is nitrogen, $R^4$ is absent and/or when $Y_2$ is nitrogen $R^3$ is absent;

$R^5$ independently in each occurrence is selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl, cyano, and halogen; and n is an integer from 1 to 10.

In some embodiments for compounds comprising Formula (I), X is selected from the group consisting of oxygen and sulfur. In some alternatives of the embodiments, X is sulfur. In exemplary alternatives of the embodiments, X is oxygen.

In some embodiments for compounds comprising Formula (I), n may be 1, 2, 3, 4, 5, 6, 7, 8, 9 or 10. In some alternatives of the embodiments, n is an integer from 1 to 6. In preferred alternatives of the embodiments, n is 3.

For each of the foregoing embodiments for compounds comprising Formula (I), $R^1$, $R^2$, $R^3$, $R^4$, $R^6$, $R^7$, $R^8$, $R^9$ and $R^{10}$ may each be independently selected from the group consisting of hydrogen, hydroxyl, aldehyde, haloformyl, hydroperoxyl, alkyl, alkenyl, substituted alkenyl, alkynyl, substituted alkynyl, aryl, substituted aryl, halogen, amino, phosphor, sulfhydryl, sulfino, sulfo, and cyano, and $R^5$ independently in each occurrence is selected from the group consisting of hydrogen, hydroxyl, aldehyde, haloformyl, hydroperoxyl, halogen, amino, phosphor, sulfhydryl, sulfino, sulfo, alkyl, and cyano.

In some alternatives of the embodiments, $R^1$ is selected from the group consisting of alkyl, substituted alkyl, amine, and aminoalkyl. In one embodiment, $R^1$ may be selected from the group consisting of alkyl and substituted alkyl. In various iterations, $R^1$ may be lower alkyl, which is defined herein as $C_1$-$C_6$. In another embodiment, $R^1$ may be aminoalkyl. In yet another embodiment, $R^1$ may be amine.

In other alternatives of the embodiments, $R^2$ is selected from the group consisting of hydrogen and alkyl. In various iterations, $R^2$ may be hydrogen. In other iterations, $R^2$ may be lower alkyl, which is defined in this iteration as $C_1$-$C_4$.

In yet other alternatives of the embodiments, $R^3$ is selected from the group consisting alkyl, halogen and cyano. In various iterations, $R^3$ may be lower alkyl, which is defined herein as $C_1$-$C_6$. In an embodiment, $R^3$ may be halogen. In another embodiment, $R^3$ may be cyano.

In other alternatives of the embodiments, $R^4$ is selected from the group consisting alkyl and halogen. In various iterations, $R^4$ may be lower alkyl, which is defined herein as $C_1$-$C_6$. In an embodiment, $R^4$ may be halogen.

In other alternatives of the embodiments, $R^6$, $R^7$, $R^8$, $R^9$ and $R^{10}$ are each independently selected from the group consisting of hydrogen and halogen. In various iterations, $R^6$, $R^7$, $R^8$, $R^9$ and $R^{10}$ are each independently selected from the group consisting of hydrogen and chlorine.

In some embodiments, $R^1$, $R^2$, $R^3$ and $R^4$ are each independently selected from the group consisting of hydrogen, alkyl, substituted alkyl, amine, aminoalkyl, halogen and cyano; $R^5$ independently in each occurrence is selected from the group consisting of hydrogen, hydroxyl, and alkyloxy; and $R^6$, $R^7$, $R^8$, $R^9$ and $R^{10}$ are each independently selected from the group consisting of hydrogen and halogen.

In some embodiments, $R^1$ is selected from the group consisting of methyl, ethyl, propyl, amino, and {—}$CH_2NH_2$; $R^2$ is selected from the group consisting of hydrogen, methyl, and ethyl; $R^3$ is selected from the group consisting of methyl, ethyl, propyl, halogen and cyano; $R^4$ is selected from the group consisting of hydrogen, methyl, ethyl and halogen; $R^5$ independently in each occurrence is selected from the group consisting of hydrogen and hydroxyl; and $R^6$, $R^7$, $R^8$, $R^9$ and $R^{10}$ are each independently selected from the group consisting of hydrogen and chlorine.

In an aspect, the disclosure provides a compound of Formula (I) wherein: X is selected from the group consisting of oxygen and sulfur; $Y_1$ and $Y_2$ are independently selected from the group consisting of carbon and nitrogen; $R^1$ is selected from the group consisting of hydrogen, $C_1$-$C_6$ alkyl, aminoalkyl, and amino; $R^2$ is selected from the group consisting of hydrogen and $C_1$-$C_4$ alkyl; $R^3$ is selected from the group consisting of absent, hydrogen, $C_1$-$C_6$ alkyl, halogen and cyano; $R^4$ is selected from the group consisting of absent, hydrogen, $C_1$-$C_6$ alkyl and halogen; $R^5$ independently in each occurrence is selected from the group consisting of hydrogen and hydroxyl; and $R^6$, $R^7$, $R^8$, $R^9$ and $R^{10}$ are each independently selected from the group consisting of hydrogen and halogen.

In another aspect, the disclosure provides a compound of Formula (I) wherein: X is oxygen; $Y_1$ and $Y_2$ are independently selected from the group consisting of carbon and nitrogen; $R^1$ is selected from the group consisting of hydrogen, $C_1$-$C_6$ alkyl, aminoalkyl, and amino; $R^2$ is selected from the group consisting of hydrogen and $C_1$-$C_4$ alkyl; $R^3$ is selected from the group consisting of absent, hydrogen, $C_1$-$C_6$ alkyl, halogen and cyano; $R^4$ is selected from the group consisting of absent, hydrogen, $C_1$-$C_6$ alkyl and halogen; $R^5$ independently in each occurrence is selected from the group consisting of hydrogen and hydroxyl; and $R^6$, $R^7$, $R^8$, $R^9$ and $R^{10}$ are each independently selected from the group consisting of hydrogen and halogen.

In still another aspect, the disclosure provides a compound of Formula (I) wherein: X is oxygen; $Y_1$ and $Y_2$ are independently selected from the group consisting of carbon and nitrogen; $R^1$ is selected from the group consisting of hydrogen, methyl, ethyl, propyl, aminoalkyl, and amino; $R^2$ is selected from the group consisting of hydrogen, methyl and ethyl; $R^3$ is selected from the group consisting of absent, hydrogen, methyl, ethyl, propyl, halogen and cyano; $R^4$ is selected from the group consisting of absent, hydrogen, methyl, ethyl and halogen; $R^5$ independently in each occurrence is selected from the group consisting of hydrogen and hydroxyl; and $R^6$, $R^7$, $R^8$, $R^9$ and $R^{10}$ are each independently selected from the group consisting of hydrogen and halogen.

In still yet another aspect, the disclosure provides a compound of Formula (I) wherein: X is oxygen; $Y_1$ is nitrogen and $Y_2$ is carbon; $R^1$ is selected from the group consisting of methyl, ethyl, propyl, aminoalkyl, and amino; $R^2$ is selected from the group consisting of hydrogen, methyl and ethyl; $R^3$ is selected from the group consisting of methyl, ethyl, propyl, halogen and cyano; $R^4$ is absent; $R^5$ independently in each occurrence is selected from the group consisting of hydrogen and hydroxyl; and $R^6$, $R^7$, $R^8$, $R^9$ and $R^{10}$ are each independently selected from the group consisting of hydrogen and halogen.

In a different aspect, the disclosure provides a compound of Formula (I) wherein: X is oxygen; $Y_1$ is carbon and $Y_2$ is nitrogen; $R^1$ is hydrogen; $R^2$ is selected from the group consisting of hydrogen and methyl; $R^3$ is absent; $R^4$ is selected from the group consisting of hydrogen, methyl, ethyl and halogen; $R^5$ independently in each occurrence is selected from the group consisting of hydrogen and hydroxyl; and $R^6$, $R^7$, $R^8$, $R^9$ and $R^{10}$ are each independently selected from the group consisting of hydrogen and halogen.

In some embodiments, compounds of the disclosure comprise a compound of Formula (II):

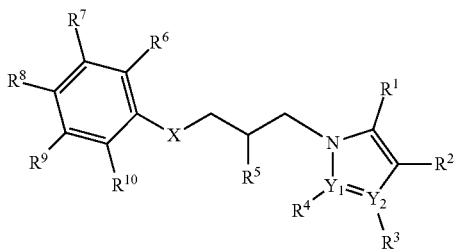

(II)

wherein:

X is selected from the group consisting of oxygen, sulfur, sulfoxide, sulfone, and nitrogen;

$Y_1$ and $Y_2$ are independently selected from the group consisting of carbon and nitrogen;

$R^1$, $R^2$, $R^3$, $R^4$, $R^6$, $R^7$, $R^8$, $R^9$ and $R^{10}$ are each independently selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl, and cyano, with the proviso that when $Y_1$ is nitrogen, $R^4$ is absent and/or when $Y_2$ is nitrogen $R^3$ is absent; and $R^5$ is selected from the group consisting of hydrogen, hydrocarbyl, substituted hydrocarbyl, hydroxyl, aldehyde, haloformyl, hydroperoxyl, halogen, amino, phosphor, sulfhydryl, sulfino, sulfo, $C_1$-$C_6$ alkyl, and cyano.

For each of the foregoing embodiments for compounds comprising Formula (II), $R^1$ may be selected from the group consisting of alkyl, substituted alkyl, amine, and aminoalkyl. In one embodiment, $R^1$ is selected from the group consisting of alkyl and substituted alkyl. In various iterations, $R^1$ may be lower alkyl, which is defined herein as $C_1$-$C_6$. In another embodiment, $R^1$ may be aminoalkyl. In yet another embodiment, $R^1$ may be amine. In some embodiments, $R^1$ is selected from the group consisting of methyl, ethyl, propyl, amino, and {—}CH2NH2.

For each of the foregoing embodiments for compounds comprising Formula (II), $R^2$ may be selected from the group consisting of hydrogen and alkyl. In various iterations, $R^2$ may be hydrogen. In other various iterations, $R^2$ may be lower alkyl, which is defined in this iteration as $C_1$-$C_4$. In some embodiments, $R^2$ is selected from the group consisting of hydrogen, methyl, and ethyl.

For each of the foregoing embodiments for compounds comprising Formula (II), $R^3$ may be selected from the group consisting of hydroxyl, alkyl, alkenyl, substituted alkenyl, alkynyl, substituted alkynyl, halogen and cyano. In some embodiments, $R^3$ is alkyl. In various iterations, $R^3$ may be lower alkyl, which is defined herein as $C_1$-$C_6$. In some embodiments, $R^3$ is selected from the group consisting of methyl, ethyl, propyl, halogen and cyano.

For each of the foregoing embodiments for compounds comprising Formula (II), $R^4$ may be selected from the group consisting alkyl and halogen. In some embodiments, $R^4$ may be lower alkyl, which is defined herein as $C_1$-$C_6$. In an embodiment, $R^4$ may be halogen. In another embodiment, $R^4$ may be selected from the group consisting of hydrogen, methyl, ethyl and halogen For each of the foregoing embodiments for compounds comprising Formula (II), $R^5$ is selected from the group consisting of hydrogen and hydroxyl.

For each of the foregoing embodiments for compounds comprising Formula (II), $R^6$, $R^7$, $R^8$, $R^9$ and $R^{10}$ are each independently selected from the group consisting of hydrogen and halogen. In various iterations, $R^6$, $R^7$, and $R^9$ may be hydrogen. In various iterations, $R^6$ and $R^{10}$ may each be independently selected from the group consisting of hydrogen and halogen. In some embodiments, $R^6$, $R^7$, and $R^9$ are hydrogen, and $R^8$ and $R^{10}$ are each independently selected from the group consisting of hydrogen and chlorine.

In an aspect, the disclosure provides a compound of Formula (II) wherein: X is selected from the group consisting of oxygen and sulfur; $Y_1$ and $Y_2$ are independently selected from the group consisting of carbon and nitrogen; $R^1$ is selected from the group consisting of hydrogen, $C_1$-$C_6$ alkyl, aminoalkyl, and amino; $R^2$ is selected from the group consisting of hydrogen and $C_1$-$C_4$ alkyl; $R^3$ is selected from the group consisting of absent, hydrogen, $C_1$-$C_6$ alkyl, halogen and cyano; $R^4$ is selected from the group consisting of absent, hydrogen, $C_1$-$C_6$ alkyl and halogen; $R^5$ is selected from the group consisting of hydrogen and hydroxyl; and $R^6$, $R^7$, $R^8$, $R^9$ and $R^{10}$ are each independently selected from the group consisting of hydrogen and halogen.

In another aspect, the disclosure provides a compound of Formula (II) wherein: X is oxygen; $Y_1$ and $Y_2$ are independently selected from the group consisting of carbon and nitrogen; $R^1$ is selected from the group consisting of hydrogen, $C_1$-$C_6$ alkyl, aminoalkyl, and amino; $R^2$ is selected from the group consisting of hydrogen and $C_1$-$C_4$ alkyl; $R^3$ is selected from the group consisting of absent, hydrogen, $C_1$-$C_6$ alkyl, halogen and cyano; $R^4$ is selected from the group consisting of absent, hydrogen, $C_1$-$C_6$ alkyl and halogen; $R^5$ is selected from the group consisting of hydrogen and hydroxyl; and $R^6$, $R^7$, $R^8$, $R^9$ and $R^{10}$ are each independently selected from the group consisting of hydrogen and halogen.

In still another aspect, the disclosure provides a compound of Formula (II) wherein: X is oxygen; $Y_1$ and $Y_2$ are independently selected from the group consisting of carbon and nitrogen; $R^1$ is selected from the group consisting of hydrogen, methyl, ethyl, propyl, aminoalkyl, and amino; $R^2$ is selected from the group consisting of hydrogen, methyl and ethyl; $R^3$ is selected from the group consisting of absent, hydrogen, methyl, ethyl, propyl, halogen and cyano; $R^4$ is selected from the group consisting of absent, hydrogen, methyl, ethyl and halogen; $R^5$ is hydroxyl; and $R^6$, $R^7$, $R^8$, $R^9$ and $R^{16}$ are each independently selected from the group consisting of hydrogen and halogen.

In still yet another aspect, the disclosure provides a compound of Formula (II) wherein: X is oxygen; $Y_1$ is nitrogen and $Y_2$ is carbon; $R^1$ is selected from the group consisting of methyl, ethyl, propyl, aminoalkyl, and amino; $R^2$ is selected from the group consisting of hydrogen, methyl and ethyl; $R^3$ is selected from the group consisting of methyl, ethyl, propyl, halogen and cyano; $R^4$ is absent; $R^5$ is hydroxyl; and $R^6$, $R^7$, $R^8$, $R^9$ and $R^{10}$ are each independently selected from the group consisting of hydrogen and halogen.

In a different aspect, the disclosure provides a compound of Formula (II) wherein: X is oxygen; $Y_1$ is carbon and $Y_2$ is nitrogen; $R^1$ is hydrogen; $R^2$ is selected from the group consisting of hydrogen and methyl; $R^3$ is absent; $R^4$ is selected from the group consisting of hydrogen, methyl, ethyl and halogen; $R^5$ is hydroxyl; and $R^6$, $R^7$, $R^8$, $R^9$ and $R^{10}$ are each independently selected from the group consisting of hydrogen and halogen.

In exemplary embodiments, compounds of the present disclosure comprise a compound selected from the group of compounds in Table A.

TABLE A

III
(DPP; Mol-5)

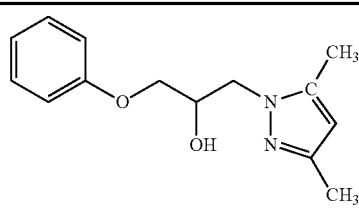

IV

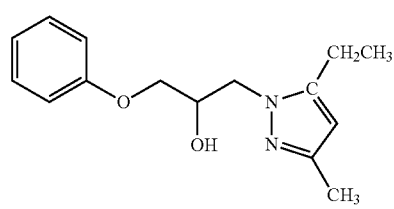

TABLE A-continued

V

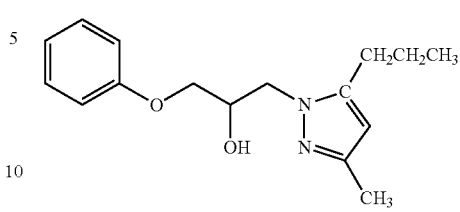

VI

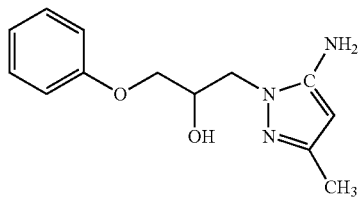 [SMILES: Cc1cc(N)n(CC(O)COc2ccccc2)n1]

VII

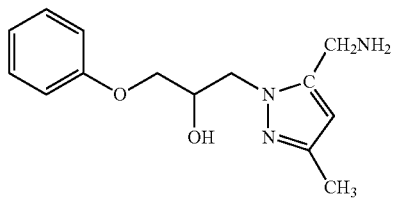

VIII

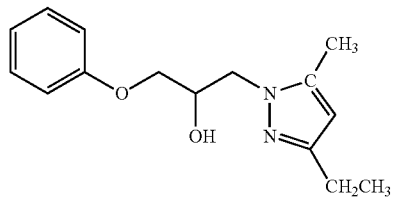 [SMILES: CCc1cc(C)n(CC(O)COc2ccccc2)n1]

IX

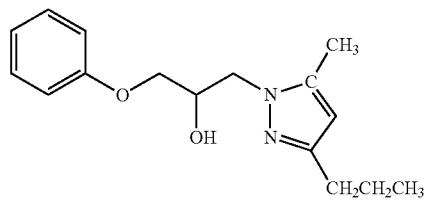

X

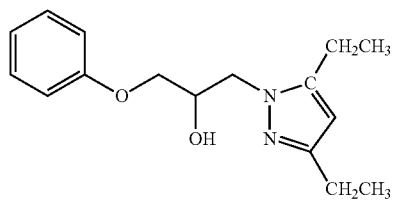 [SMILES: CCc1cc(CC)n(CC(O)COc2ccccc2)n1]

XI

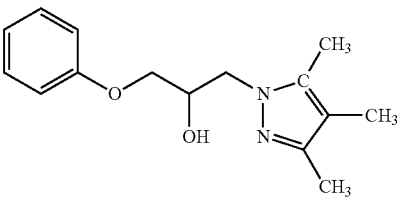 [SMILES: Cc1nn(CC(O)COc2ccccc2)c(C)c1C]

TABLE A-continued

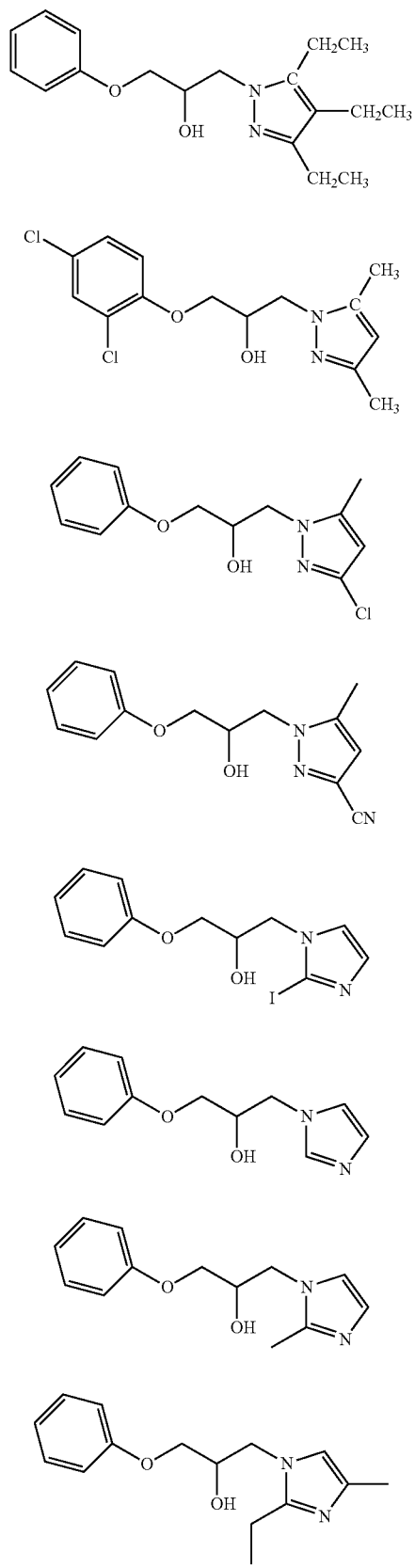

In some embodiments, compounds of the disclosure comprise a compound of Formula (XX):

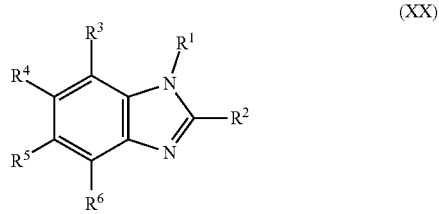

wherein:
$R^1$, $R^2$, $R^3$, $R^4$, $R^5$ and $R^6$ are each independently selected from the group consisting of hydrogen, hydrocarbyl, substituted hydrocarbyl, hydroxyl, aldehyde, haloformyl, hydroperoxyl, halogen, amino, phosphor, sulfhydryl, sulfino, and sulfo.

In an aspect, the disclosure provides a compound of Formula (XX) wherein: $R^3$, $R^4$, $R^5$ and $R^6$ are hydrogen and $R^1$ and $R^2$ are independently selected from the group consisting of hydrocarbyl, substituted hydrocarbyl, alkyl, substituted alkyl, alkenyl, substituted alkenyl, alkynyl, substituted alkynyl, aryl, substituted aryl, aminoalkyl, substituted aminoalkyl, amidoalkyl and substituted amidoalkyl.

In another aspect, the disclosure provides a compound of Formula (XX) wherein: $R^3$, $R^4$, $R^5$ and $R^6$ are hydrogen and $R^1$ and $R^2$ are independently selected from the group consisting of alkyl, substituted alkyl, alkenyl, substituted alkenyl, alkynyl, substituted alkynyl, aryl, substituted aryl, aminoalkyl, substituted aminoalkyl, amidoalkyl and substituted amidoalkyl.

In still another aspect, the disclosure provides a compound of Formula (XX) wherein: $R^3$, $R^4$, $R^5$ and $R^6$ are hydrogen and $R^1$ and $R^2$ are independently selected from the group consisting of alkyl, substituted alkyl, aminoalkyl, substituted aminoalkyl, amidoalkyl and substituted amidoalkyl.

In still yet another aspect, the disclosure provides a compound of Formula (XX) wherein: $R^3$, $R^4$, $R^5$ and $R^6$ are hydrogen; $R^1$ is selected from the group consisting of alkyl and substituted alkyl; and $R^2$ is selected from the group consisting of alkyl, substituted alkyl, aminoalkyl, substituted aminoalkyl, amidoalkyl and substituted amidoalkyl.

In a different aspect, the disclosure provides a compound of Formula (XX) wherein: $R^3$, $R^4$, $R^5$ and $R^6$ are hydrogen; $R^1$ is selected from the group consisting of a $C_1$-$C_6$ alkyl and substituted $C_1$-$C_6$ alkyl; and $R^2$ is selected from the group consisting of alkyl, substituted alkyl, aminoalkyl, substituted aminoalkyl, amidoalkyl and substituted amidoalkyl.

In another different aspect, the disclosure provides a compound of Formula (XX) wherein: $R^3$, $R^4$, $R^5$ and $R^6$ are hydrogen; $R^1$ is selected from the group consisting of a $C_1$-$C_6$ alkyl, —$(CH_2)_n$OH, —$(CH_2)_n$NH$_2$, and a $C_1$-$C_6$ alkyl terminally substituted with a heteroatom, wherein n is independently an integer from 1 to 6; and $R^2$ is selected from the group consisting of alkyl, substituted alkyl, aminoalkyl, substituted aminoalkyl, amidoalkyl and substituted amidoalkyl.

In still another different aspect, the disclosure provides a compound of Formula (XX) wherein: $R^3$, $R^4$, $R^5$ and $R^6$ are hydrogen; $R^1$ is selected from the group consisting of a $C_1$-$C_6$ alkyl, —$(CH_2)_n$OH, —$(CH_2)_n$NH$_2$, and a $C_1$-$C_6$ alkyl terminally substituted with a heteroatom, wherein n is independently an integer from 1 to 6; and $R^2$ is selected from the group consisting of aminoalkyl, substituted aminoalkyl, amidoalkyl and substituted amidoalkyl.

In still yet another different aspect, the disclosure provides a compound of Formula (XX) wherein: $R^3$, $R^4$, $R^5$ and $R^6$ are hydrogen; $R^1$ is selected from the group consisting of a $C_1$-$C_6$ alkyl, —$(CH_2)_n$OH, —$(CH_2)_n$NH$_2$, and a $C_1$-$C_6$ alkyl terminally substituted with a heteroatom; and $R^2$ is selected from the group consisting of —$(CH_2)_n$NHCO$(CH_2)_n$OH, wherein n is independently an integer from 1 to 6.

In other aspects, the disclosure provides a compound of Formula (XX) wherein: $R^3$, $R^4$, $R^5$ and $R^6$ are hydrogen; $R^1$ is selected from the group consisting of a $C_1$-$C_6$ alkyl; and $R^2$ is selected from the group consisting of aminoalkyl, substituted aminoalkyl, amidoalkyl and substituted amidoalkyl.

In still other aspects, the disclosure provides a compound of Formula (XX) wherein: $R^3$, $R^4$, $R^5$ and $R^6$ are hydrogen; $R^1$ is selected from the group consisting of a $C_1$-$C_6$ alkyl; and $R^2$ is selected from the group consisting of —$(CH_2)_n$NHCO$(CH_2)_n$OH, wherein n is independently an integer from 1 to 6.

In an exemplary embodiment, a compound of Formula (XX) is:

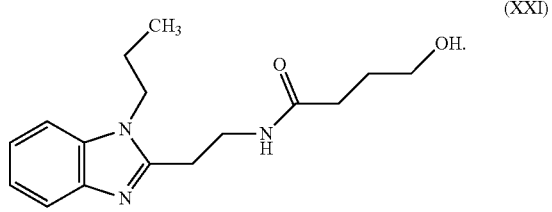 [SMILES: CCCn1c(CCNC(=O)CCCO)nc2ccccc21]

(XXI)

In general, compounds of the disclosure bind the lectin-like oxidized low-density lipoprotein (ox-LDL) receptor-1 (LOX-1). The term "binding" as used herein refers to an affinity between two molecules, for example, a small molecule compound and a target protein such as LOX-1. While not wishing to be bound by theory, compounds of the disclosure may bind the LOX-1 binding site, thereby blocking binding of ox-LDL to LOX-1, inhibiting LOX-1-mediated uptake of ox-LDL, and combinations thereof.

In some embodiments, binding affinity of a compound to LOX-1 may be determined using purified LOX-1 protein or a fragment thereof. Methods of determining binding affinity of a compound with a purified protein are known in the art. Non-limiting examples of methods of determining binding affinity of a compound with a purified protein may include surface plasmon resonance and thermal shift assay. Purified LOX-1 may be produced by methods known in the technical field of the instant disclosure, such as recombinant technology, chemical synthesis, and cell culture, or by modified methods thereof.

In one alternative of the embodiments, binding of a compound to LOX-1 is determined using purified LOX-1 protein and surface plasmon resonance. In another alternative of the embodiment, the affinity of binding of a compound to LOX-1 is measured using purified LOX-1 protein and thermal shift assay. In general, a thermal shift assay is a thermal-denaturation assay that measures the thermal stability of a target protein and a subsequent increase in protein melting temperature due to the binding of a ligand to the protein. In a preferred embodiment, interaction of a compound with LOX-1 is measured using purified LOX-1 protein and a thermal shift assay as described in the Examples. Using this assay, a compound of the disclosure may bind a purified LOX-1 protein and increase the melting temperature of the LOX-1 protein by about 2, 3, 4, 5, 6, 7, 8, 9, 10, 11, 12, 13, 14, 15, 16, 17, 18, 19, 20, 25, or about 30° C. or more due to the binding of a ligand to the protein. In some embodiments, a compound of the disclosure increases the melting temperature of the LOX-1 protein by about 2, 3, 4, 5, or about 6° C. In other embodiments, a compound of the disclosure increases the melting temperature of the LOX-1 protein by about 5, 6, 7, 8, 9, or about 10° C. In yet other embodiments, a compound of the disclosure increases the melting temperature of the LOX-1 protein by about 9, 10, 11, 12, 13, 14, or about 15° C. In other embodiments, a compound of the disclosure increases the melting temperature of the LOX-1 protein by about 15, 16, 17, 18, 19, 20, 25, or about 30° C. or more. In preferred embodiments, a compound of the disclosure increases the melting temperature of the LOX-1 protein by about 9, 10, 11, 12, 13, or about 14° C.

Binding of a compound of the present disclosure to LOX-1 inhibits LOX-1 activity in a cell. Non-limiting examples of LOX-1 activity in a cell that may be inhibited by a compound of the present disclosure include binding and uptake of ox-LDL into the cell and intracellular signaling of LOX-1. As such, inhibition of LOX-1 activity by a compound of the present disclosure may be determined by contacting a cell expressing LOX-1 with a compound of the present disclosure and monitoring LOX-1 activity. For instance, a cell expressing LOX-1 may be contacted with a compound of the present disclosure in vitro to determine inhibition of LOX-1 activity.

Many cell types may be suitable for this assay. A cell expressing LOX-1 may be a primary cell line derived from a cell normally expressing LOX-1. Non-limiting examples of a cell normally expressing LOX-1 may include macrophages, endothelial cells, monocytes, platelets, smooth muscle cells, cardiomyocytes, and brain cells. Methods of preparing a primary cell line utilize standard techniques known to individuals skilled in the art. In some embodiments, a cell expressing LOX-1 is a macrophage. In other embodiments, a cell expressing LOX-1 is an endothelial cell.

Alternatively, a cell expressing LOX-1 may be an established cell line genetically modified to express LOX-1. A cell line may be adherent or non-adherent, or a cell line may be grown under conditions that encourage adherent, non-adherent or organotypic growth using standard techniques known to individuals skilled in the art. A cell line may be contact inhibited or non-contact inhibited. Non-limiting examples of cell lines that may be genetically modified to express LOX-1 include Chinese hamster ovary cells (CHO), vero African green monkey kidney cells, mouse SVEC4 vascular endothelial cells, human umbilical vein endothelial cells (HUVECs), and HeLa cells. In some embodiments, a cell expressing LOX-1 is a transgenic CHO cell genetically modified to express LOX-1.

In some embodiments, a compound of the present disclosure inhibits binding and uptake of ox-LDL into a cell expressing LOX-1. For instance, inhibition of binding and uptake of ox-LDL into a cell may be assayed by monitoring uptake of a labeled ox-LDL into a cell expressing LOX-1 in the presence or absence of a compound of the disclosure. Non-limiting examples of suitable labels include fluorescent labels, chemiluminescent labels, radioactive labels, colorimetric labels, and resonance labels. Methods of labeling peptides are well known in the art. In some embodiments, inhibition of binding and uptake of ox-LDL into a cell is assayed using a chemiluminescently-labeled ox-LDL. In other embodiments, inhibition of binding and uptake of ox-LDL into a cell is assayed using a radioactively-labeled ox-LDL. In yet other embodiments, inhibition of binding and uptake of ox-LDL into a cell is assayed using a colorimetricly-labeled ox-LDL. In other embodiments, inhibition of binding and uptake of ox-LDL into a cell is assayed using ox-LDL labeled with resonance labels. In preferred embodiments, inhibition of binding and uptake of ox-LDL into a cell is assayed using a fluorescently-labeled ox-LDL (Dil-ox-LDL). In exemplary embodiments, inhibition of binding and uptake of ox-LDL into a cell is assayed using a fluorescently-labeled ox-LDL as described in the Examples. Using this assay, a compound of the present disclosure may inhibit uptake of ox-LDL into a cell expressing LOX-1 by about 10, 15, 20, 25, 30, 35, 40, 45, 50, 55, 60, 65, 70, 75, 80, 85, 90, 95, or about 100% in the presence of 20 nM of the compound. In one embodiment, a compound of the present disclosure inhibits uptake of ox-LDL into a cell expressing LOX-1 by about 10, 15, 20, 25, or about 30% in the presence of 20 nM of the compound. In another embodiment, a compound of the present disclosure inhibits uptake of ox-LDL into a cell expressing LOX-1 by about 30, 35, 40, 45, or about 50% in the presence of 20 nM of the compound. In yet another embodiment, a compound of the present disclosure inhibits uptake of ox-LDL into a cell expressing LOX-1 by about 50, 55, 60, 65, or about 70% in the presence of 20 nM of the compound. In yet another embodiment, a compound of the present disclosure inhibits uptake of ox-LDL into a cell expressing LOX-1 by about 70, 75, 80, 85, or about 90% in the presence of 20 nM of the compound. In another embodiment, a compound of the present disclosure inhibits uptake of ox-LDL into a cell expressing LOX-1 by about 85, 90, 95, or about 100% in the presence of 20 nM of the compound. In a preferred embodiment, a compound of the present disclosure inhibits uptake of ox-LDL into a cell expressing LOX-1 by about 20, 25, 30, 35, or about 40% in the presence of 20 nM of the compound.

In other embodiments, a compound of the present disclosure inhibits intracellular signaling of LOX-1 in a cell. Non-limiting examples of intracellular signaling of LOX-1 in a cell include NF-κB activation, superoxide generation, eNOS deficiency, increased monocyte adhesion to endothelial cells, phosphorylation of p44/42 MAP kinase and p38 MAP kinase, and expression of E-selectins, P-selectins, NADPH oxidase, VCAM-1, ICAM-1, and LOX-1. In one alternative of the embodiments, a compound of the present disclosure inhibits NF-κB activation. In another alternative of the embodiments, a compound of the present disclosure inhibits superoxide generation. In yet another alternative of the embodiments, a compound of the present disclosure inhibits eNOS deficiency. In an additional alternative of the embodiments, a compound of the present disclosure inhibits increased monocyte adhesion to endothelial cells. In one alternative of the embodiments, a compound of the present disclosure inhibits phosphorylation of p44/42 MAP kinase. In another alternative of the embodiments, a compound of the present disclosure inhibits phosphorylation of p38 MAP kinase. In yet another alternative of the embodiments, a compound of the present disclosure inhibits expression of E-selectins. In another alternative of the embodiments, a compound of the present disclosure inhibits expression of P-selectins. In an additional alternative of the embodiments, a compound of the present disclosure inhibits expression of NADPH oxidase. In another alternative of the embodiments, a compound of the present disclosure inhibits expression of VCAM-1. In yet another alternative of the embodiments, a compound of the present disclosure inhibits expression of ICAM-1. In an additional alternative of the embodiments, a compound of the present disclosure inhibits expression of LOX-1.

Titration curves measuring the ability of a compound to inhibit LOX-1 activity may also be performed to determine the $IC_{50}$. In some embodiments, the $IC_{50}$ of a compound may be less than about 300, 250, 200, 150, 100, 50, 10, or about 1 nM.

A composition of the disclosure may be formulated and administered to a subject by several different means as described in Section II.

II. Composition

In another aspect, the disclosure provides a composition comprising compounds of the disclosure. Compounds may be as described in Section I above.

Compounds may be incorporated into pharmaceutical compositions suitable for in vivo, in vitro, in situ, or ex vivo use. Such compositions typically comprise a compound of the disclosure and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with a compound, use thereof in the compositions is contemplated. Supplementary active compounds may also be incorporated into the compositions.

A pharmaceutical composition of the disclosure may be formulated to be compatible with its intended route of administration. Examples of routes of administration include parenteral, e.g., intravenous, intradermal, subcutaneous, oral (e.g., inhalation), transdermal (topical), transmucosal, and rectal administration. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. Parenteral preparations may be enclosed in ampoules, disposable syringes, or multiple dose vials made of glass or plastic.

Pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In all cases, a composition may be sterile and may be fluid to the extent that easy syringeability exists. A composition may be stable under the conditions of manufacture and storage and may be preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressed container or dispenser which contains a suitable propellant, e.g., a gas such as carbon dioxide, or a nebulizer.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. Compounds may also be prepared in the form of suppositories (e.g., with conventional suppository bases such as cocoa butter and other glycerides) or retention enemas for rectal delivery.

Compounds may be prepared with carriers that will protect a compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. These may be prepared according to methods known to those skilled in the art, for example, as described in U.S. Pat. No. 4,522,811.

III. Method of Use

In an aspect, the disclosure provides a method of inhibiting ox-LDL uptake in a cell. The method comprises contacting LOX-1 with a composition comprising a compound of the disclosure. Inhibiting ox-LDL uptake is described in more detail in Section I. The disclosure also provides a method of reducing LOX-1 expression in a cell. The method comprises contacting LOX-1 with a composition comprising a compound of the disclosure. A reduction in LOX-1 expression may be measured by a reduction in LOX-1 protein expression or LOX-1 nucleic acid expression. Methods of measuring protein and nucleic acid expression are well known in the art. Non-limiting examples include immunoblots, flow cytometry, immunohistochemistry, and various other epitope binding agent methods useful for evaluating protein expression, and PCR useful for evaluating nucleic acid expression. LOX-1 expression is reduced if the ratio of the level of expression of LOX-1 in the presence of compound as compared with the expression level of LOX-1 in the absence of compound is less than 1.0. For example, a ratio less than 1, 0.8, 0.6, 0.4, 0.2, 0.1, 0.05, 0.001 or less. In another embodiment, the reduction in expression is measured using p-value. For instance, when using p-value, LOX-1 expression is reduced when the p-value of LOX-1 in the presence of compound as compared with the expression level of LOX-1 in the absence of compound is less than 0.1, preferably less than 0.05, more preferably less than 0.01, even more preferably less than 0.005, the most preferably less than 0.001.

In another aspect, the disclosure provides a method of reducing the number of monocytes adhered to a cell. The method comprises contacting LOX-1 with a composition comprising a compound of the disclosure. A reduction in the number of monocytes adhered to a cell may be due to a reduction in VCAM-1 expression on the cell. A compound of the disclosure reduces the expression of VCAM-1 on a cell thereby reducing the number of monocytes adhered to the cell. A reduction in the number of monocytes adhered to a cell limits the number of monocytes available for transformation into foam cells. A reduction in the number of foam cells limits the buildup of an atherosclerotic plaque. The concept of "reduction" as described above may also be applied here. Accordingly, the disclosure also provides a method of reducing buildup of atherosclerotic plaques. The method comprising administering a composition comprising a compound of the disclosure to a subject.

In still another aspect, the disclosure provides a method of inhibiting LOX-1 activity. A method of the disclosure comprises contacting LOX-1 with a compound of the disclosure to inhibit LOX-1. LOX-1 has specific affinity and is the predominant scavenger receptor for ox-LDL. As described above, inhibiting LOX-1 activity using a compound of the disclosure inhibits uptake of ox-LDL into the cell and intracellular signaling of LOX-1. Inhibition of intracellular signaling may be measured by evaluating activation of ERK1/2, P38 MAPK, and/or other MAP kinases. An inhibition of intracellular signaling of LOX-1 results in inhibition of or reduced phosphorylation of ERK1/2, P38 MAPK, and/or other MAP kinases. Additional indicators of inhibition of intracellular activity are described in Section I.

By inhibiting LOX-1 activity, a method of the disclosure may be used to treat any clinical condition that may result from LOX-1 activity and elevated levels of ox-LDL. Non-limiting examples of a condition that may result from LOX-1 activity or elevated levels of ox-LDL include atherosclerosis, clinical conditions resulting from metabolic syndrome, thrombocytopenia, diabetic nephropathy, sepsis, osteoarthritis, rheumatoid arthritis, kidney disease, myocardial injury initiated during ischemia-reperfusion, inflammatory reactions after percutaneous transluminal coronary recanalization (PTCR) or percutaneous transluminal coronary angioplasty (PTCA), vascular restenosis after PTCA and PTCR, thrombogenesis in blood vessels, and increased susceptibility to diabetes. As used herein, "treating a clinical condition" refers to preventing the development of a clinical condition, preventing the progression of a clinical condition, and/or reducing the severity of a clinical condition.

In some embodiments, a method of the disclosure may be used to treat increased susceptibility to diabetes. In other embodiments, a method of the disclosure may be used to treat thrombocytopenia. In yet other embodiments, a method of the disclosure may be used to treat diabetic nephropathy. In other embodiments, a method of the disclosure may be used to treat sepsis. In additional embodiments, a method of the disclosure may be used to treat osteoarthritis. In other embodiments, a method of the disclosure may be used to treat rheumatoid arthritis. In even more embodiments, a method of the disclosure may be used to treat kidney disease. In additional embodiments, a method of the disclosure may be used to treat inflammatory reactions after percutaneous transluminal coronary recanalization (PTCR) or percutaneous transluminal coronary angioplasty (PTCA). In some embodiments, a method of the disclosure may be used to treat vascular restenosis after PTCA and PTCR. In other embodiments, a method of the disclosure may be used to treat thrombogenesis in blood vessels.

In some preferred embodiments, a method of the disclosure may be used to treat myocardial injury initiated during ischemia-reperfusion. Myocardial I/R injury is associated with thrombolysis, angioplasty, and coronary bypass surgery. Injury to myocardium due to I/R includes cardiac contractile dysfunction, arrhythmias, and irreversible myocyte damage, including both apoptotic and necrotic cell death.

In other preferred embodiments, a method of the disclosure may be used to treat atherosclerosis. In yet other preferred embodiments, a method of the disclosure may be used to treat clinical conditions resulting from metabolic syndrome.

Typically, a compound of the disclosure is formulated for in vivo, in vitro, in situ, or ex vivo use as described in Section II above. In some embodiments, a compound of the disclosure is formulated for in vivo use, and administered to a subject. The term "subject," as used herein, refers to an animal. The subject may be an embryo, a juvenile, or an adult. Suitable animals include vertebrates such as mammals, birds, reptiles, amphibians, and fish. Examples of suitable mammals include, without limit, rodents, companion animals, livestock, and primates. Non-limiting examples of rodents include mice, rats, hamsters, gerbils, and guinea pigs. Suitable companion animals include, but are not limited to, cats, dogs, rabbits, hedgehogs, and ferrets. Non-limiting examples of livestock include horses, goats, sheep, swine, cattle, llamas, and alpacas. Suitable primates include, but are not limited to, humans, capuchin monkeys, chimpanzees, lemurs, macaques, marmosets, tamarins, spider monkeys, squirrel monkeys, and vervet monkeys. Non-limiting examples of birds include chickens, turkeys, ducks, and geese. An exemplary subject is a mouse. Another exemplary subject is a human.

In other embodiments, a cell contacted by a composition of the disclosure is an in vitro cell line. Cell lines may be as described in Section I above. In other embodiments, a cell may be contacted by a composition of the disclosure ex vivo or in situ in a tissue sample or organ obtained from a subject. Non-limiting examples of suitable tissues include connective tissue, muscle tissue, nervous tissue, and epithelial tissue. Non-limiting examples of suitable organs include organs of the cardiovascular system, digestive system, the endocrine system, the excretory system, the immune system, the nervous system, the reproductive system, and the respiratory system. Tissue and organ samples may be cultured in vitro or ex vivo. They may also be biopsy samples or otherwise removed from a subject. In certain embodiments, a tissue or organ sample may be homogenized before contact with a composition of the disclosure.

In certain aspects, a therapeutically effective amount of a composition of the disclosure may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. It is within the skill of one in the art, to determine the route of administration based on the disease or condition to be treated.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the peptides useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the disclosure is administered to a subject. A "therapeutically effective amount" is an amount of the therapeutic composition sufficient to produce a measurable response (e.g., a reduction in symptoms, reduction in LOX-1, reduction in atherosclerotic plaques, reduction in VCAM-1, reduction in activation of MAP kinases, reduction in local presence of monocytes). Actual dosage levels of active ingredients in a therapeutic composition of the disclosure can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, disease, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

Although the foregoing methods appear the most convenient and most appropriate and effective for administration of a composition of the disclosure, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

In some embodiments, a method of protecting a cell as described herein may comprise administering a composition of the disclosure in combination with other treatment options that may be useful for treating metabolic syndrome or other conditions that may lead to endothelial dysfunction and atherosclerosis.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups:

hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted, or replaced, with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halo, heterocyclo, hydroxyl, keto, ketal, phospho, nitro, and thio.

As various changes could be made in the above compounds, products and methods without departing from the scope of the invention, it is intended that all matter contained in the above description and in the examples given below, shall be interpreted as illustrative and not in a limiting sense.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Introduction for Examples 1-8

The oxidized low-density lipoprotein receptor 1 (LOX-1) is a 32 kDa lectin-like receptor with specific affinity to oxidized LDL (ox-LDL). It is predominant in endothelial cells and is one of the major scavenger receptors in macrophages. Elevated ox-LDL is a primary component of metabolic syndrome responsible for endothelial dysfunction and initiation and progression of atherosclerosis via its interaction with LOX-1. The LOX-1 mediated downstream events are manifold and include a) internalization of ox-LDL; b) endothelial dysfunction; c) formation of foam cells; and d) stimulation of smooth muscle cell proliferation and angiogenesis. Critical involvement of ox-LDL in the development of atherosclerosis has been shown by the inventors in a number of in vivo studies utilizing various animal models and approaches including immunization against ox-LDL, removal of ox-LDL from the blood stream by liver-specific overexpression of LOX-1, and deletion of LOX-1.

Thus, LOX-1 has been proven to be a primary factor for the development of atherosclerosis. Accumulated data from the inventors and others clearly support the notion that targeting LOX-1 or LOX-1 mediated signaling is an attractive direction for the development of anti-atherogenic therapies. Moreover, LOX-1 based therapy may have much broader application beyond atherosclerosis and atherosclerosis-based cardiovascular conditions. Perturbation of lipid metabolism and ox-LDL has been shown to be implicated in higher susceptibility to diabetes. Preliminary data from the inventors also indicate that LOX-1 is one of the determinants of the extent of myocardial injury following acute myocardial infarction.

The Examples below describe the identification and development of small molecule inhibitors of LOX-1 for inhibition of LOX-1 activity and ox-LDL uptake by vascular cells. Small molecules confer several potential advantages including ease of manufacturing, possibility of oral administration and, in comparison to antibodies, more efficient tissue penetration.

Figure 1B:
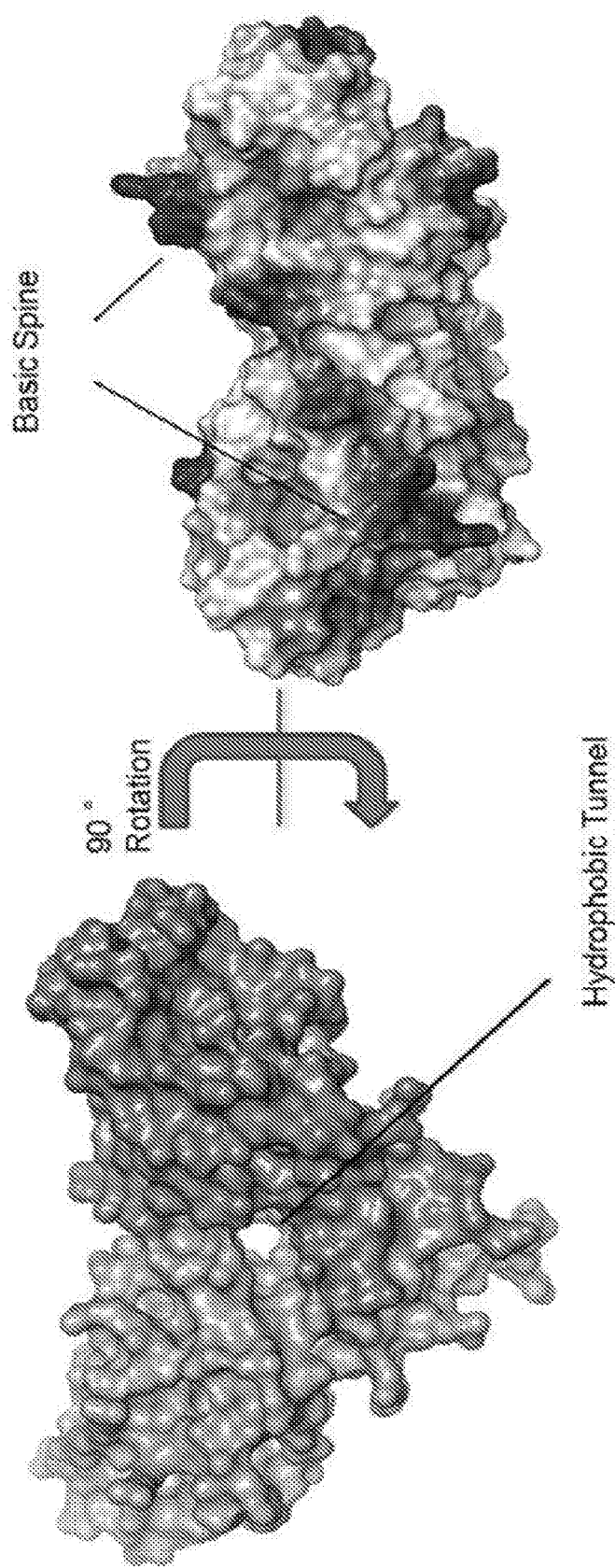

Example 1. Identification of Small Molecule Inhibitors of LOX-1 Based on LOX-1 Crystallography Data LOX-1 is a transmembrane protein comprising four domains and the C-terminal domain is responsible for ox-LDL recognition[10,11]. The crystal structure analysis of the C-terminal of human LOX-1 (FIG. 1A, FIG. 1B) suggests that it exists as homodimer with a central hydrophobic tunnel that extends through the entire molecule[12,13].

The structure of LOX-1 and its interactions with ox-LDL have been extensively studied. A model of ox-PL (phospholipid)/LOX-1 interactions predicts that the aliphatic chain at the sn-1 position of the phospholipid molecule anchors in the tunnel of the LOX-1 protein, whereas other structural components such as sn-2 carboxylic acid group and its distance to the positively charged trimethylammonium group determine the strength of the binding.

Figure 1C:
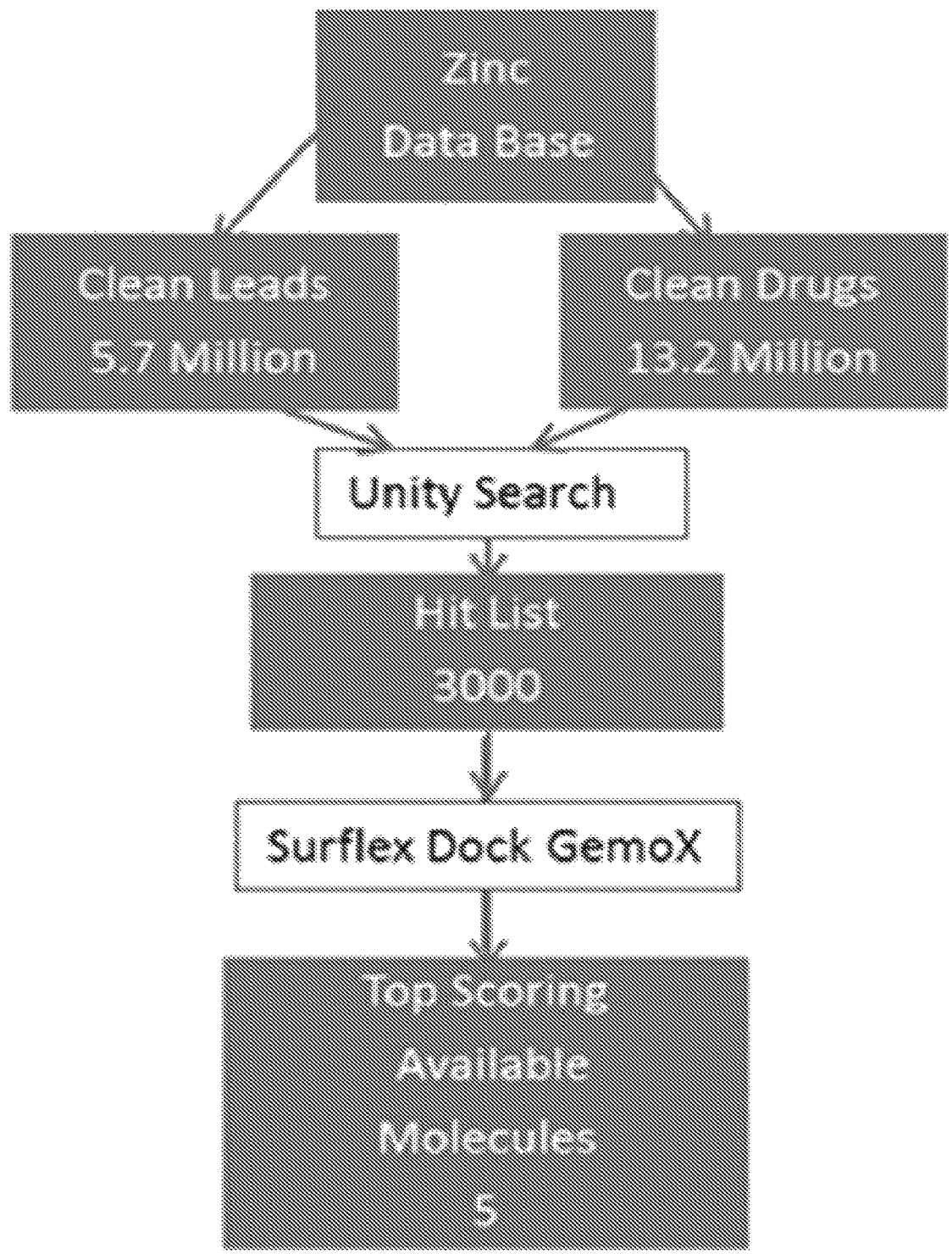

In this Example, virtual, structure-based drug design (SBDD) screening techniques using a library containing a very large number of compounds were used to identify small molecules that are likely to bind to the LOX-1 binding site and that have the potential to block LOX-1/ox-LDL interaction (FIG. 1C).

In short, the protein is first prepared for docking analysis. The coordinates of the high resolution crystal structure of LOX-1 were obtained from the Research Collaboratory for Structural Bioinformatics (RCSB) Protein Data Bank (PDB code 1YPQ). Hydrogen atoms were added and the positions optimized, and certain side chain orientations were also optimized. Partial charge and Lennard-Jones parameters from the TRIPOSE force field were applied.

Virtual screening is basically a search for complementarity of the ligands with the binding site of the protein. These searches were carried out in multiple steps. Initially a cavity analysis on LOX-1 was performed to locate the binding site. The main cavity obtained from this calculation was in agreement with the ligand binding observed in the crystal structure and with the conclusions of the modeling studies of LOX-1 with oxidized phospholipid. The second step was to define a few hydrogen bond donors and acceptors in the cavity and perform a search to identify small molecules with complementary hydrogen bonding partners and with a molecular volume that fit into the binding cavity. This step served as the initial filter, which reduced the number of molecules to a smaller set of about 3,000 from the initial set of 19 million compounds in the compound libraries (FIG. 1C).

Figure 2A:
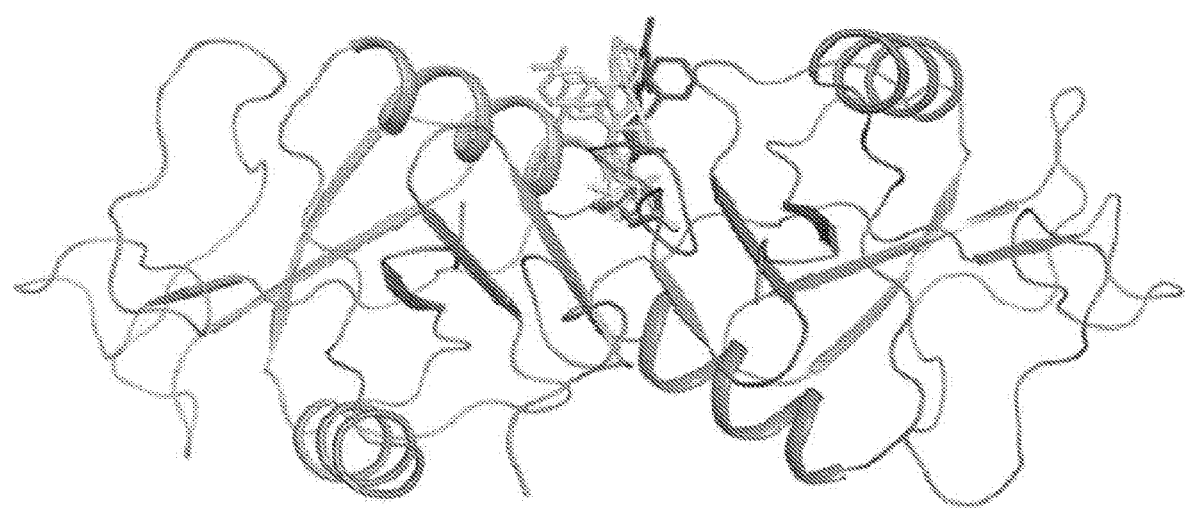

These calculations assigned probability scores for good binding for each of these molecules. Initially, 20 molecules with the top scores were picked for further analysis. A number of the computer-selected molecules contained peptide bonds and consequently could be degraded by proteases in the body. Therefore, most molecules with peptide bonds were discarded from the list, but a few with very high scores were retained. Despite the chances of degradation, these molecules can provide insights when the crystal structures of the complexes are analyzed. The final list comprised of 11 compounds, five of which were used for biological studies (Table 1). FIG. 2A and FIG. 2B show simulated binding interactions in the tunnel of LOX-1 structure.

TABLE 1

Lead Compounds.

| Notation | Structure | Vendor Information |
|---|---|---|
| Mol-1 | [structure] | Molport Riga, Latvia |
| Mol-2 | [structure] | Enamine, Monmouth Jct., NJ |
| Mol-3 | [structure] | Mcule Inc., Palo Alto, CA |
| Mol-4 | [structure] | Mcule Inc., Palo Alto, CA |
| Mol-5 | [structure] | Mcule Inc., Palo Alto, CA |

Example 2. Effect of Lead Compounds on Thermal Stability of LOX-1 Protein

As the next step, a protein assay was performed to assess the interaction of the lead compounds with LOX-1 protein for an additional confirmation of the binding to LOX1. The extracellular domain of LOX-1 was expressed and the protein was purified. Using the purified protein, a thermal shift assay was performed. The technique involves measuring thermal denaturation temperatures of the protein in the presence and absence of inhibitors. A larger shift in thermal denaturation is indicative of a tight binding of the ligand to the protein.

In short, the thermal shift assay was performed using a real-time PCR detection system with the fluorescent dye sypro orange to monitor protein unfolding. Fluorescence increases upon protein unfolding because sypro orange has higher quantum in lower dielectric medium and low quantum in higher dielectric medium. During the thermal shift assay a protein exposes the hydrophobic region which corresponds to a lower dielectric environment. The thermal shift assay instrument contains accurate temperature control devices and a CCD detector for simultaneous imaging of fluorescence changes in the microplate. The typical reaction volume of a thermal shift assay is 20 µl, which includes the protein solution, the test compound solution, and the sypro orange. The temperature in the real-time PCR machine during the thermal shift assay was ramped 0.5° C./minute till 100° C.

Figure 2C:
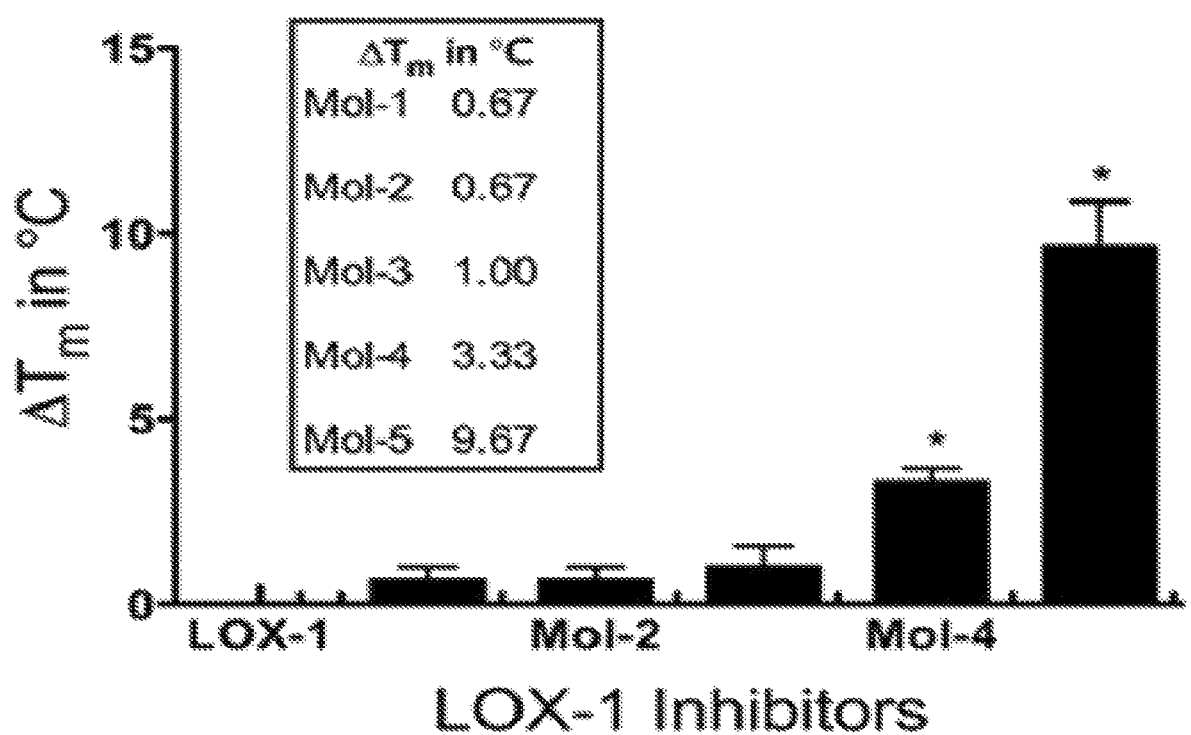

The five lead compounds were tested for their effect on the thermal stability of LOX-1 protein. Of five molecules tested Mol-5 and Mol-4 showed significant shifts (4° and 10° shifts, respectively) (FIG. 2C).

Example 3. Effect of Lead Compounds on Ox-LDL Uptake by HUVECs

Figure 3A:
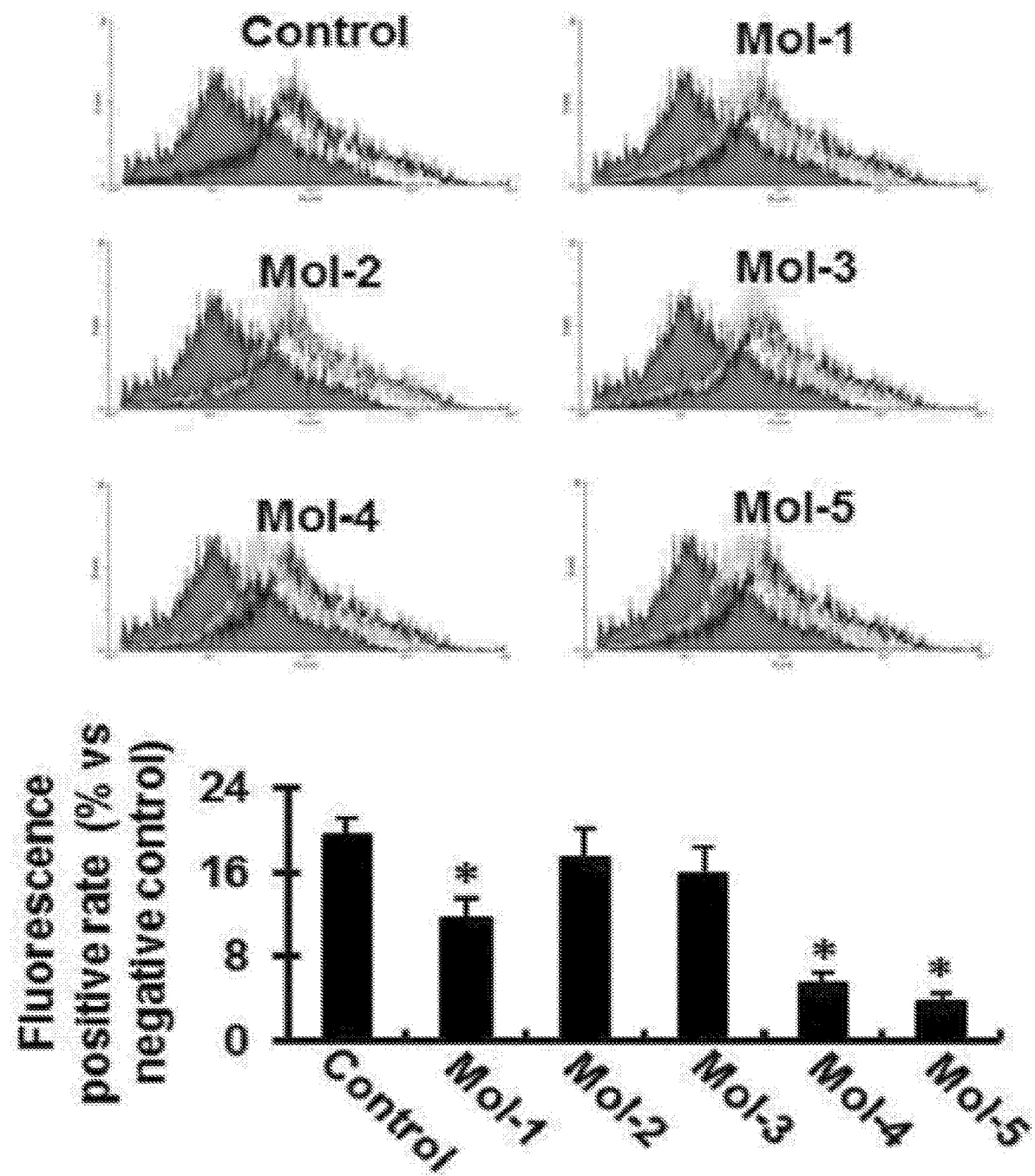
FIG. 3A, FIG. 3B, FIG. 3C and FIG. 3D depict the inhibitory effect of the lead compounds on Dil-ox-LDL uptake by HUVECs and CHO cells (measured by flow cytometry) and the effect of the lead compounds on ox-LDL-induced LOX-1 mRNA and protein expression.
Figure 3B:
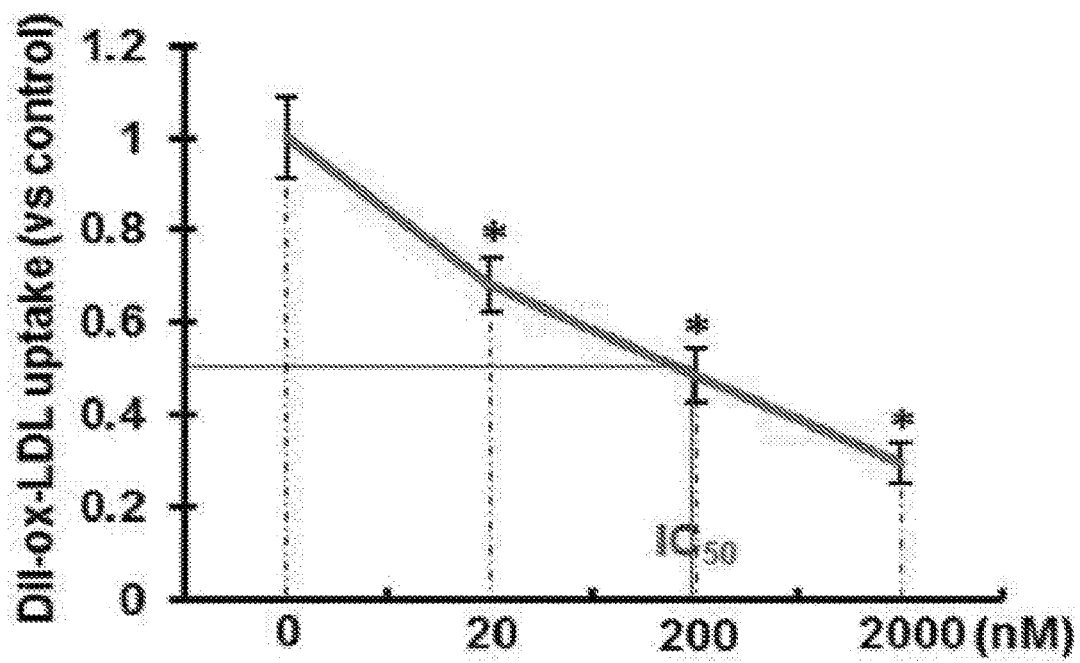
Figure 5:
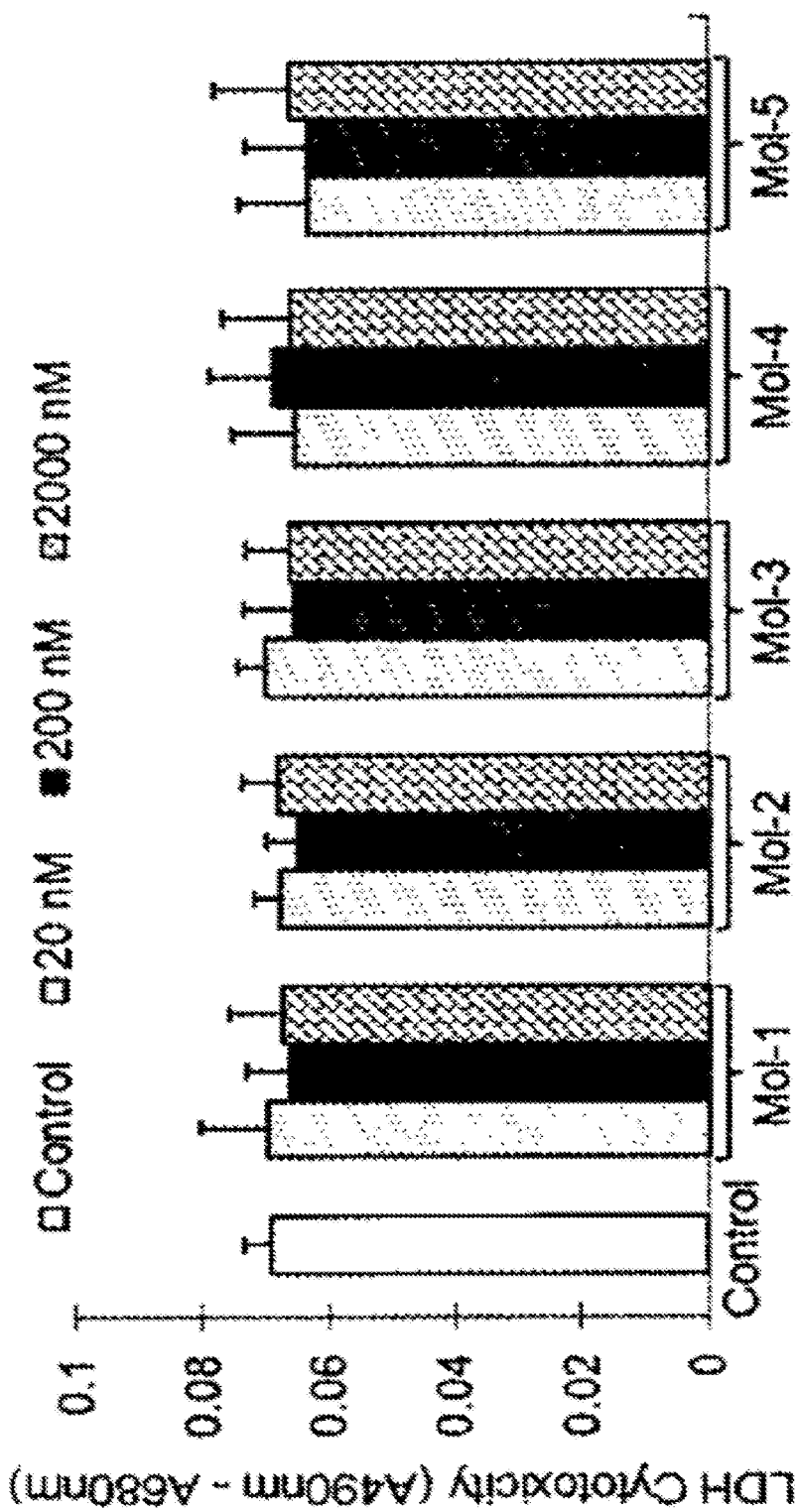
FIG. 5 depicts a graph showing the absence of cytotoxicity (measured with a Pierce LDH cytotoxicity assay kit (ThermoFisher Scientific) after exposure of HUVECs to compounds in three different concentrations (20, 200 and 2000 nM) for 6.5 hours.
Figure 6A:
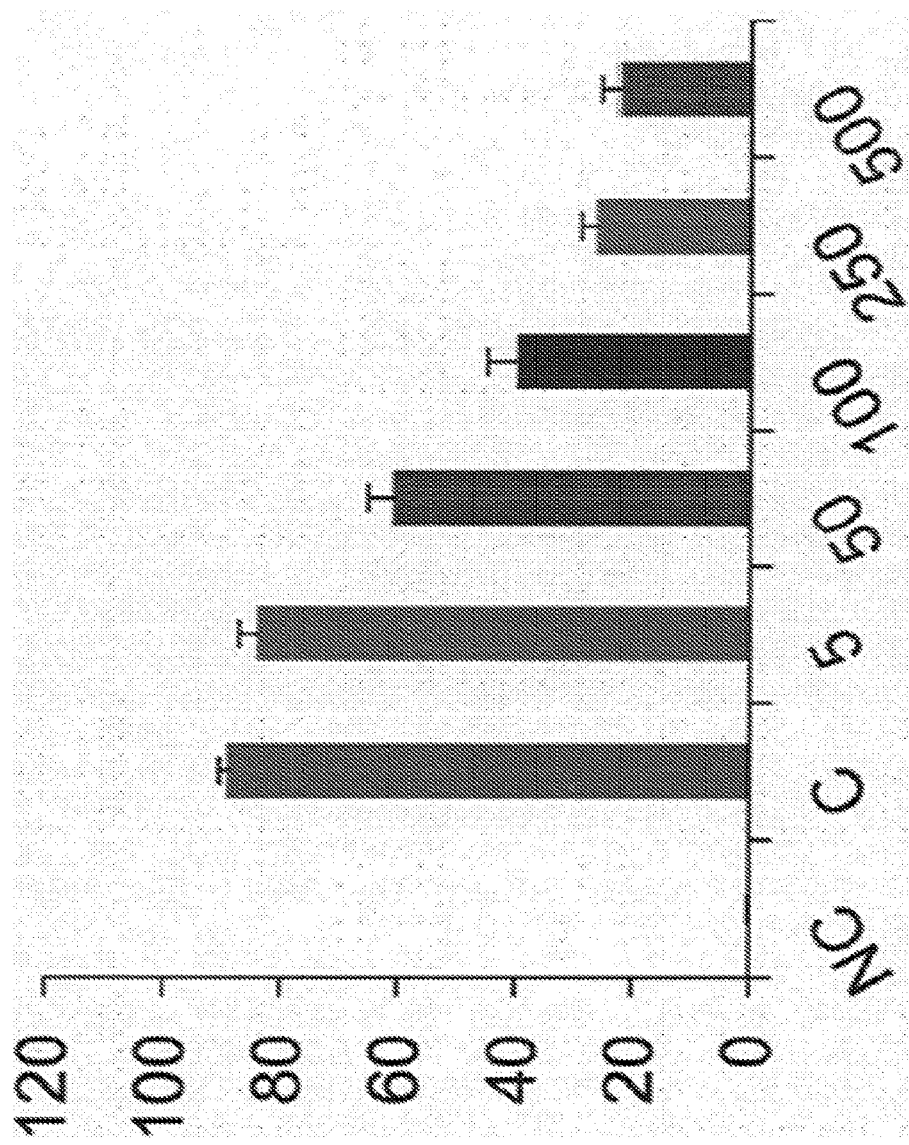
FIG. 6A depicts the $IC_{50}$ for Mol-5. The x-axis represents Mol-5 concentration (nM) and the y-axis represents ox-LDL uptake by ECs.
Figure 6B:
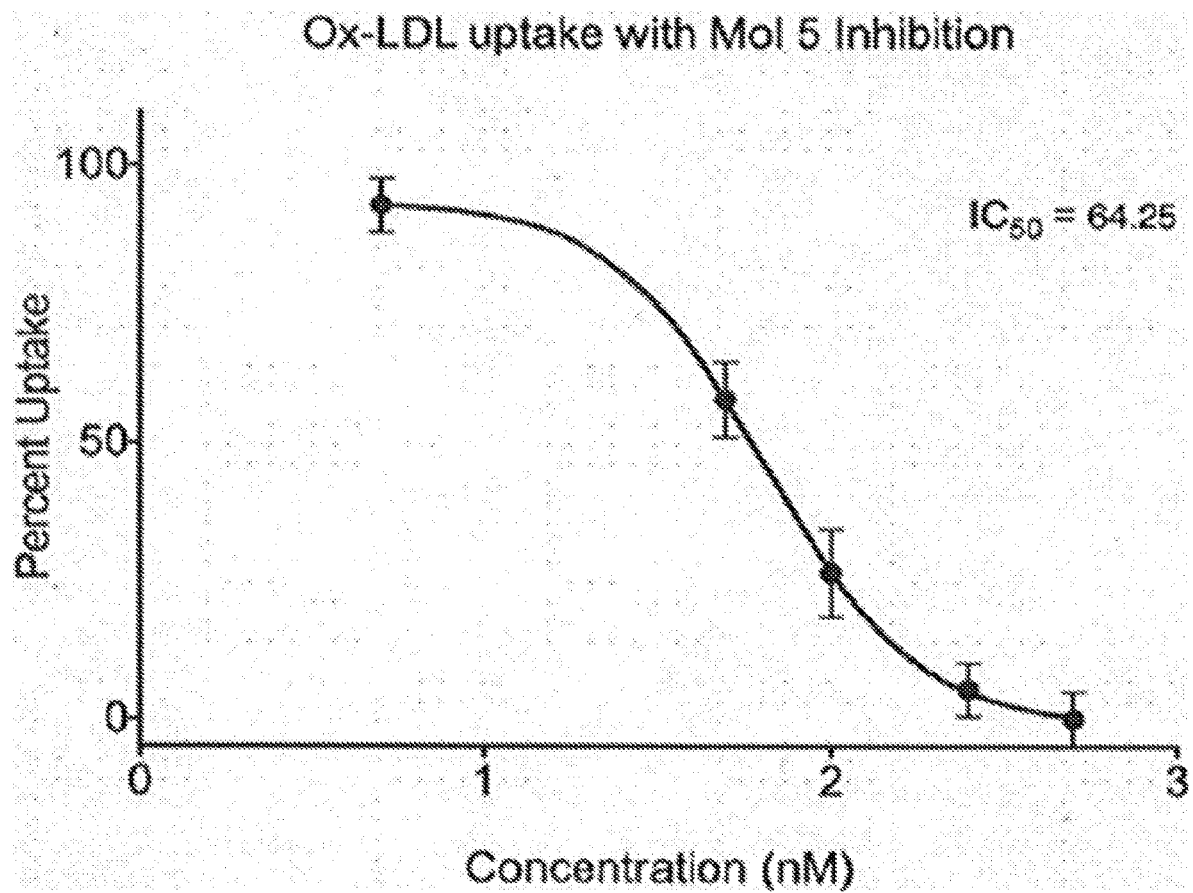
FIG. 6B depicts the ox-LDL uptake with Mol-5 inhibition. The $EC_{50}$ value is 64 nm.

For further characterization, human endothelial cells and fluorescently-labeled DiI-ox-LDL were used for measuring initiation of atherogenic process based on interaction of vascular wall with ox-LDL. Ox-LDL uptake by human umbilical vein endothelial cells (HUVECs) was measured after exposure to 200 nM of each compound using flow cytometry. As shown in FIG. 3A, Mol-5 and Mol-4 significantly and potently inhibited ox-LDL uptake (P<0.05), and Mol-1 also displayed a moderate inhibitory effect. Mol-2 and Mol-3 had no significant effect on ox-LDL uptake (P>0.05). Overall, Mol-5 exhibited the maximum inhibitory effect on ox-LDL uptake by HUVECs (FIG. 3A). The dose response to modulation of ox-LDL uptake by Mol-5 (0, 20, 200 and 2000 nM) was also measured in CHO cells overexpressing human LOX-1. As shown in FIG. 3B, Mol-5 reduced ox-LDL uptake in a dose dependent manner, with $IC_{50}$ value ~200 nM. A second dose response curve was conducted to narrow in on the effect of lower concentrations of Mol-5 on ox-LDL uptake (FIG. 6A). Using this information the $EC_{50}$ was estimated to be 64 nm (FIG. 6B). Notably, no cytotoxicity after exposure of HUVECs to the compounds at three different concentrations (20, 200 and 2000 nM) was observed (FIG. 5).

Example 4. Effect of the Lead Molecules on LOX-1 Expression in HUVECs

Figure 3C:
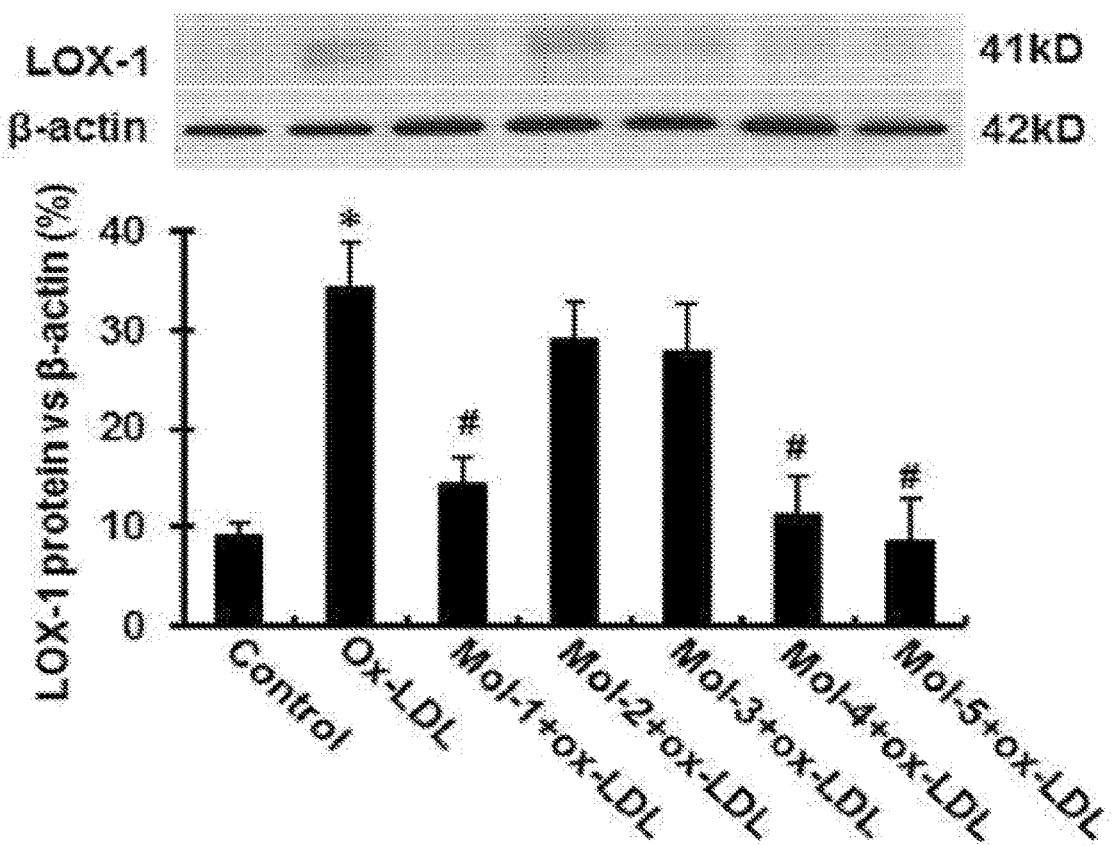

Internalization of ox-LDL via binding to LOX-1 activates endothelial cells and upregulates the expression of LOX-1[2]. In this study, it was tested if the lead molecules would inhibit LOX-1 expression. Accordingly, LOX-1 protein expression in HUVECs was measured by Western blotting. As shown in FIG. 3C, ox-LDL (5 μg/ml), as expected, markedly increased LOX-1 protein expression (P<0.01). Addition of Mol-1, Mol-4 and Mol-5, each at 200 nM concentration significantly reduced ox-LDL-induced LOX-1 protein expression (P<0.05).

Figure 3D:
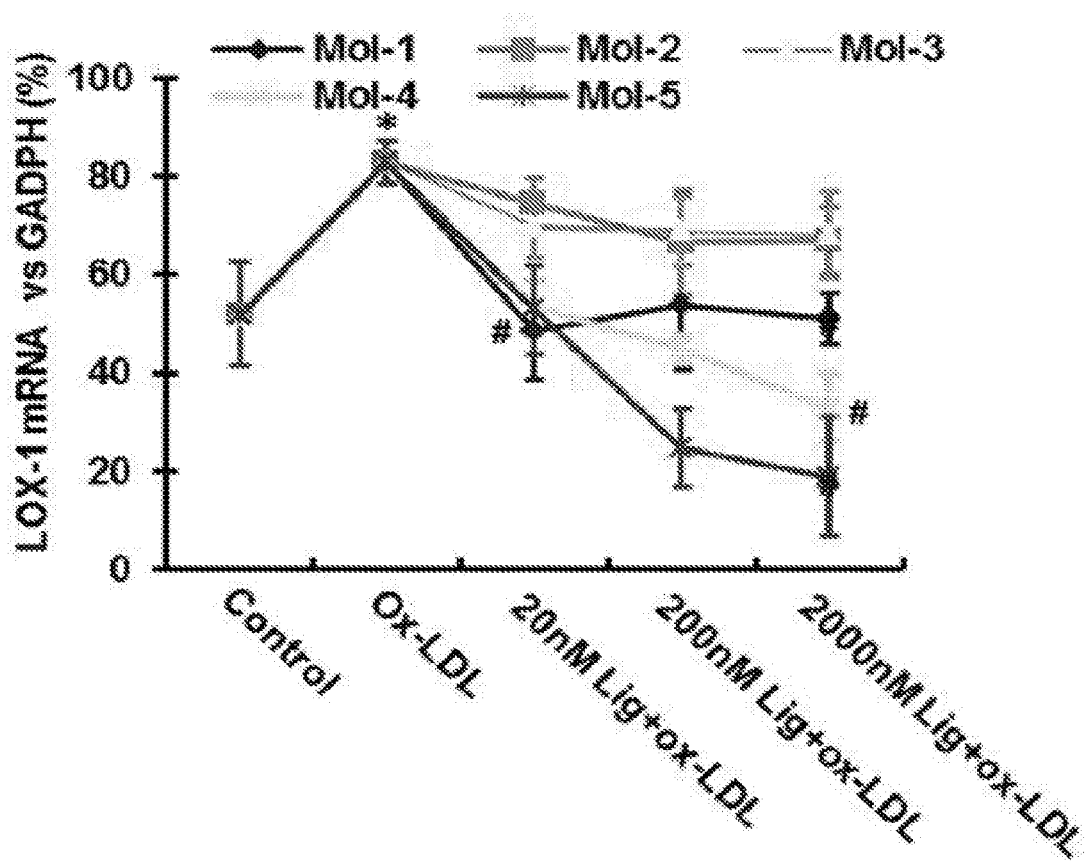

LOX-1 mRNA levels in HUVECs treated with ox-LDL in the absence or presence of the lead molecules at varying concentrations was also measured. As shown in FIG. 3D, exposure to ox-LDL (5 μg/ml for 6 h) significantly increased LOX-1 mRNA expression (P<0.05), and Mol-1, Mo-4 and Mol-5 each significantly reduced ox-LDL-induced LOX-1 mRNA upregulation (P<0.05).

Figure 4A:
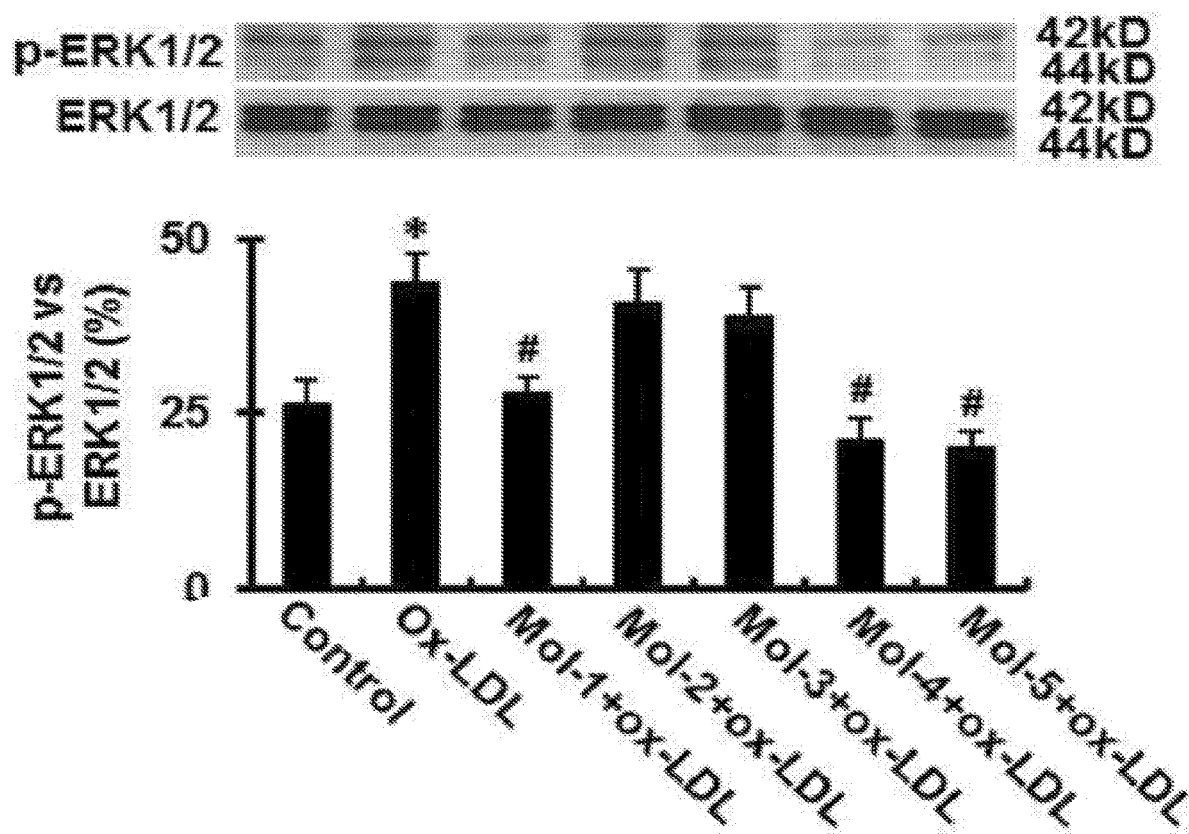
FIG. 4A, FIG. 4B, FIG. 4C, FIG. 4D and FIG. 4E depict the effect of lead molecules on ox-LDL-induced the activation of MAPKs in HUVECs, VCAM-1 expression and monocyte adhesion onto HUVECs.
Figure 4B:
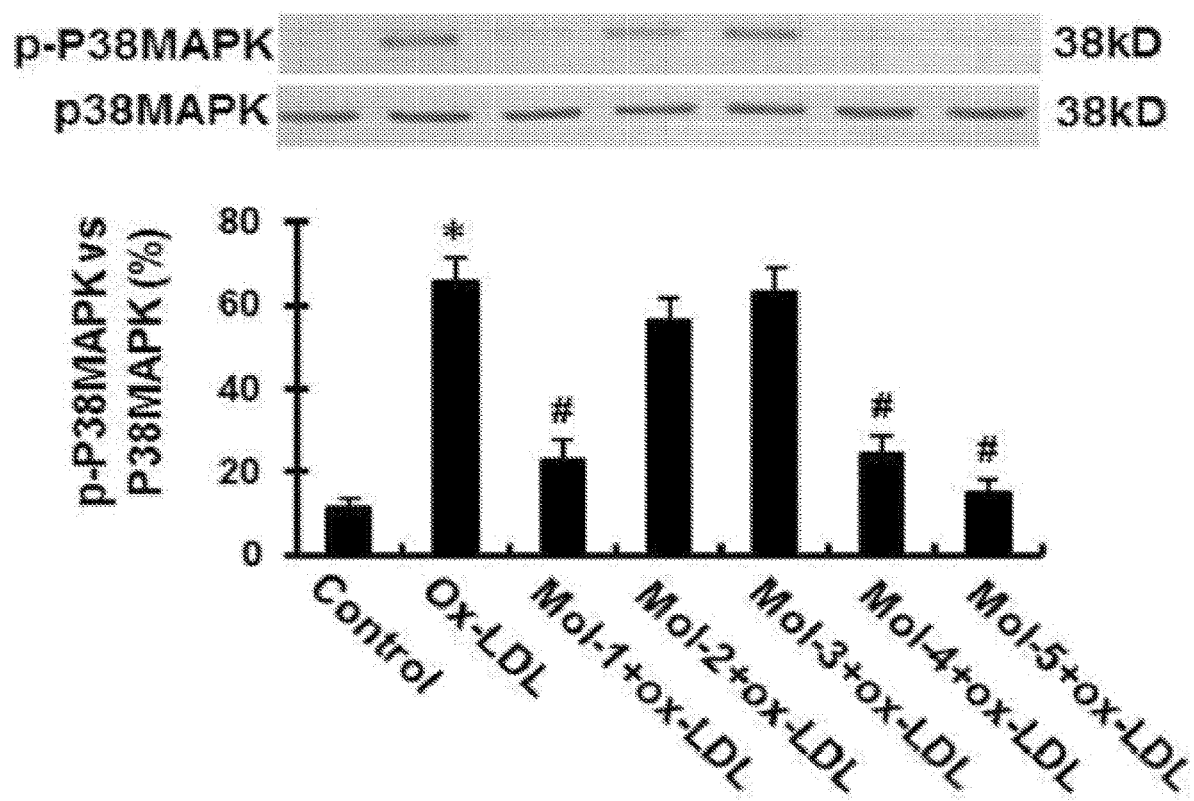

Example 5. Effect of the Lead Molecules on the Activation of MAP Kinases in HUVECs To assess downstream effects of each candidate molecule, ox-LDL induced expression and activation of ERK1/2 and P38MAPK was measured in HUVECs in the absence or presence of each candidate molecule (200 nM). As shown in FIG. 4A and FIG. 4B, Mol-1, MoL-4 and Mol-5 each significantly inhibited ox-LDL-induced activation of ERK1/2 and P38 MAPK (P<0.01 or <0.05). Of note, Mol-5 exhibited the maximum inhibition of activation of MAP kinases, and Mol-2 and Mol-3 had no significant effect on ox-LDL-induced activation of MAPKs. Importantly, unphosphorylated MAPKs were not affected by any of the candidate molecules.

Example 6. Effect of the Lead Molecules on VCAM-1 Expression in HUVECs

Figure 4C:
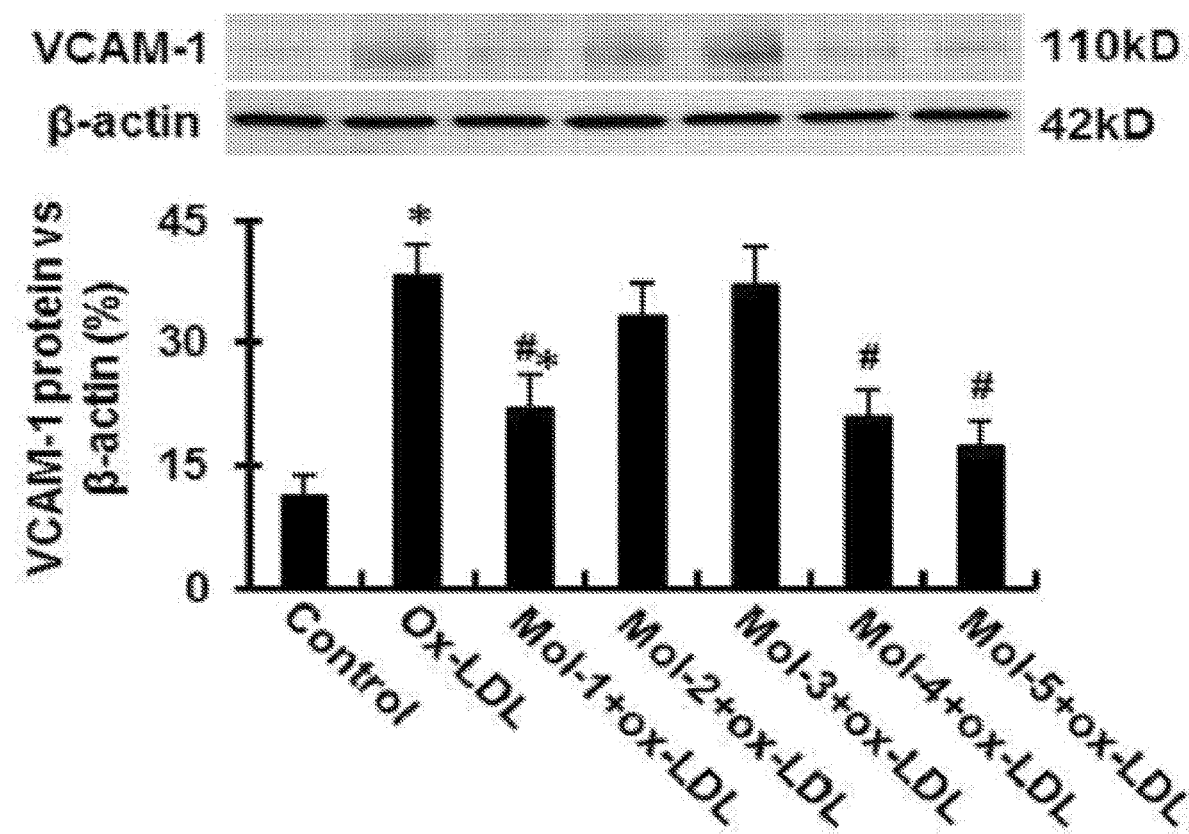
Figure 4D:
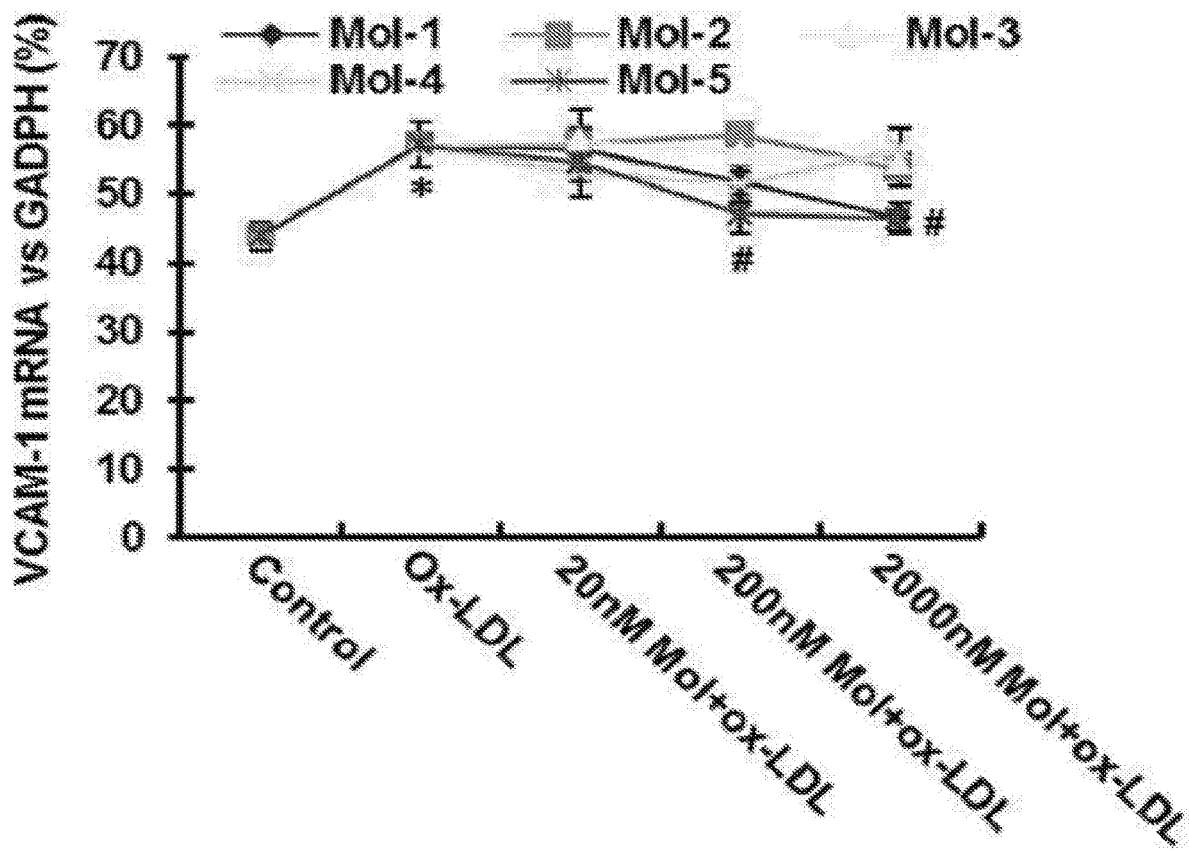

It is known that the activation of LOX-1 by ox-LDL in endothelial cells stimulates the expression of leukocyte adhesion molecules[26]. In this study, VCAM-1 expression in HUVECs in the presence of 5 μg/ml ox-LDL was measured. As shown in FIG. 4C, exposure to ox-LDL substantially enhanced VCAM-1 protein expression, which was significantly reduced by Mol-1, MoL-4 and Mol-5 (each in 200 nM concentration) (P<0.01 vs. ox-LDL alone). VCAM-1 mRNA expression in HUVECs exposed to 5 μg/mL ox-LDL for 6 hrs was also measured. As shown in FIG. 4D, ox-LDL increased VCAM-1 mRNA expression (P<0.05), and Mol-4 and Mol-5 significantly reduced ox-LDL-mediated VCAM-1 mRNA upregulation (P<0.05).

Example 7. Effect of the Lead Molecules on Adhesion of Monocytes to HUVECs

The ox-LDL-induced expression of adhesion molecules, such as VCAM-1, facilitates the adhesion of inflammatory cells, such as monocytes. In this study, ox-LDL treatment resulted in a dramatic increase in adhesion of monocytes to HUVECs, and Mol-1, Mol-4 and Mol-5 each at 200 nM concentration decreased the number of monocytes adherent to HUVECs (FIG. 4E; P<0.01 or <0.05).

Example 8. Liver Microsomal Stability

Metabolic stability or clearance is recognized as one of the main determinants of drug concentration in blood. The metabolic stability of Mol-5 was tested using liver microsomes form mice and humans to obtain stability ranking and intrinsic clearance. Table 2 presents the half-life and intrinsic clearance values. Mol-5 displays reasonable stability in human liver microsomes, but low stability in mouse.

TABLE 2

Half-life ($t_{1/2}$) and intrinsic clearance values ($CL_{int}$) of liver microsomal stability experiment.

| Species | Compound | $t_{1/2}$ (min) | $CL_{int}$ (μl/min/mg protein) |
|---|---|---|---|
| Human | Verapamil | 10.9 ± 0.3 | 127.4 ± 3.9 |
|  | Mol-5 | 55.3 ± 2.2 | 25.1 ± 1.0 |
| Mouse | Verapamil | 3.4 ± 0.1 | 407.8 ± 6.4 |
|  | Mol-5 | 1.7 ± 0.1 | 836.3 ± 40.8 |

Discussion for the Examples 1-8

The interaction of ox-LDL with LOX-1 on endothelial cells has several consequences, such as initiation of inflammation which is an early event in atherogenesis[27-29]. Ox-LDL binding to the cell surface receptor LOX-1 leads to the internalization of ox-LDL. The presence of ox-LDL in the subendothelial space promotes transformation of monocytes to macrophages and macrophages into foam cells, and subsequently initiates buildup of atherosclerotic plaque. The endothelial cells express LOX-1 several-fold more than other scavenger receptors[30]. Therefore, it has been proposed that LOX-1 inhibition may be useful in the treatment of conditions associated with LOX-1 over-expression[9].

As described above, 5 potential inhibitors of LOX-1 have been identified by virtual screening, and the activity of these 5 compounds has been evaluated using various assays. The differential scanning fluorimetry displayed significant thermal shift with Mol-5 and Mol-4 while it did not show measurable shifts with Mol-1, Mol-2 and Mol-3. Interestingly the cell-based assays show moderate activity of Mol-1, albeit lower than that of Mol-4 and Mol-5. Thus Mol-1 showed functional activity without inducing thermal shift. Although ligand binding generally enhances thermal stability, there are exceptions to this concept and sometimes binding can take place without change in thermal stability[31]. It is possible that Mol-1 binds to LOX-1 protein and alters activity without causing a significant shift in thermal stability.

The inhibitory effect of the lead compounds on the uptake of ox-LDL by HUVECs was quantified. Mol-5 showed the most potency as it reduced the uptake of ox-LDL by 80%, and Mol-4 was somewhat less potent as it reduced the uptake of ox-LDL by 65% (FIG. 3A), both at 200 nM concentration. Mol-1 reduced the uptake of ox-LDL by about 35%. Mol-2 and Mol-3 had no significant effect on ox-LDL uptake. Of note, Mol-5 also inhibited the uptake of ox-LDL by CHO cells transfected with human LOX-1 with an $IC_{50}$ value of 200 nM (FIG. 3B). Thus, the efficacy of Mol-5 in HUVECs as well as in CHO cells was confirmed.

Ox-LDL interaction with LOX-1 stimulates the expression of LOX-1 in endothelial cells. Indeed, the exposure of HUVECs to ox-LDL in the present study resulted in ~60% increase in LOX-1 mRNA consistent with previous observations[2]. Inhibition of LOX-1 transcription by the lead compounds was assessed in three different concentrations (20, 200 and 2000 nM). It was observed that both Mol-4 and Mol-5 reduced LOX-1 transcription at 200 nM concentration by 47% and 70%, respectively, reflecting the potency of these compounds. Mol-1, Mol-2 and Mol-3 had no significant effect on LOX-1 transcription.

The interaction of ox-LDL with LOX-1 in endothelial cells results in several down-stream effects, such as phosphorylation of MAPKs (including P38 and ERK1/2). P38 MAPK activation is thought to be pro-inflammatory, whereas ERK1/2 activation is related to cell proliferation, although this functional differentiation of function is not absolute. In the present study, ox-LDL had a dramatic effect on the phosphorylation of both P38 and ERK1/2 components of MAPK. As shown in FIG. 4A and FIG. 4B, Mol-5 reduced the level of phospho-P38 MAPK by 75%, Mol-4 and Mol-1 by around 60%. Mol-5 and Mol-4 also potently reduced ERK1/2 phosphorylation, and Mol-1 reduced ERK1/2 phosphorylation moderately, whereas Mol-2 and Mol-3 had no significant effect. Of note, ox-LDL did not affect the levels of unphosphorylated ERK1/2 or P38 MAPK. The lead compounds also did not affect the levels of unphosphorylated ERK1/2 or P38 MAP K.

Figure 4E:
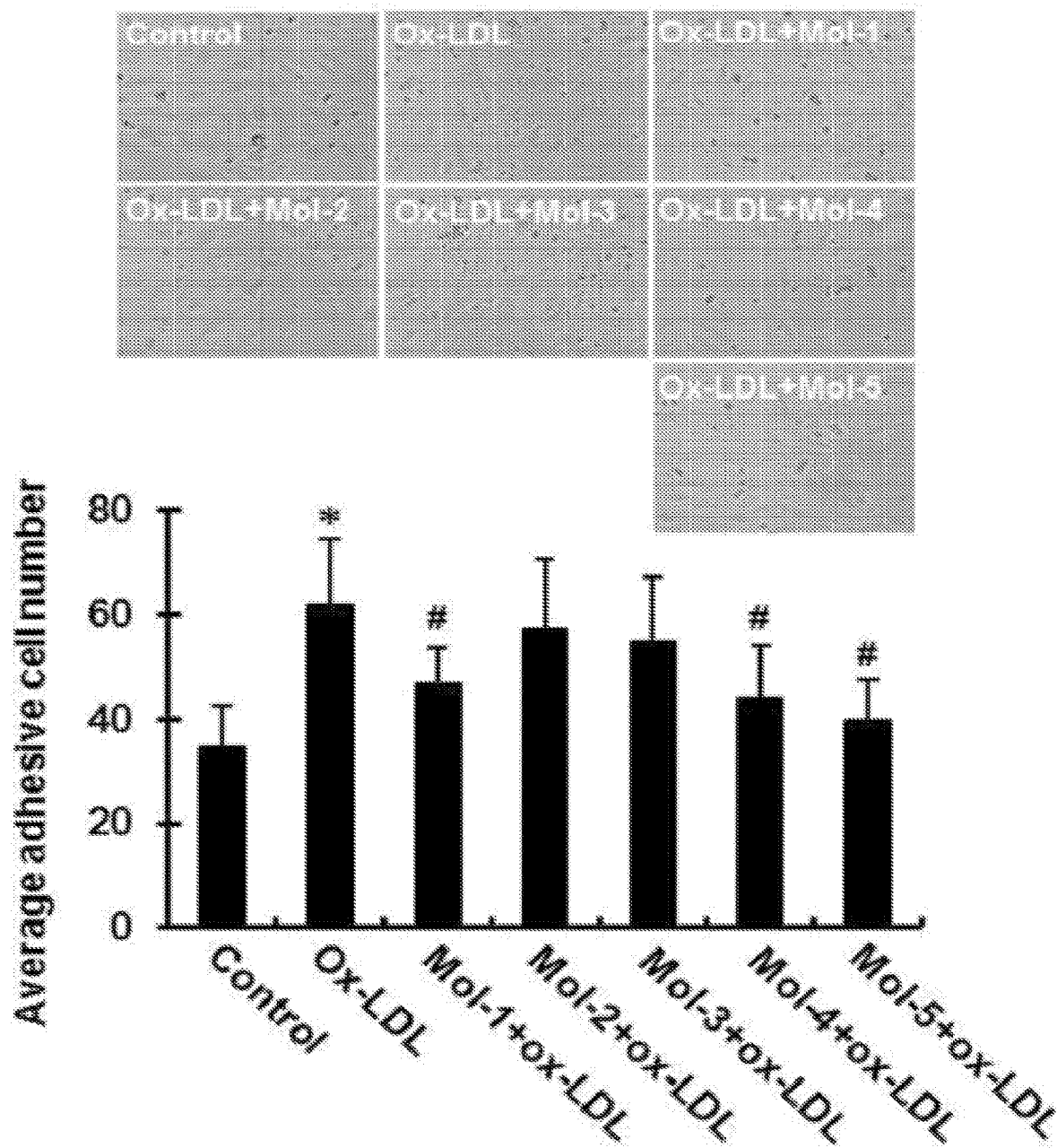

Cell based assays revealed that the interaction of ox-LDL with LOX-1 leads to intense expression of VCAM-1 at both mRNA and protein levels. Consistent with previous data on ox-LDL internalization and intracellular signaling, Mol-4 and Mol-5 significantly inhibited the expression of VCAM-1 at both mRNA and protein levels. Treatment of HUVECs with ox-LDL increased the expression of VCAM-1 several-fold, and the lead molecules significantly reduced ox-LDL-induced expression of VCAM-1 (both m RNA and protein). As expected, VCAM-1 upregulation was associated with intense monocyte adhesion to HUVECs, and Mol-5, Mol-4 and Mol-1 each reduced monocyte adhesion significantly (by 35%, 30% and 25%, respectively) (FIG. 4E).

Since these molecules could potentially be used clinically, we estimated their cytotoxicity, and observed almost no toxicity until at least 2000 nM concentration.

A number of new medications under development are biologics. Anti-hLOX-1 antibody has also been developed[32] and it may prove to be effective in the treatment of atherosclerosis and related disorders. However, immunogenicity remains a limitation of antibody therapy[33]. Chemical inhibitors of LOX-1 may be equally effective as biologics without major side-effects.

As mentioned earlier, several laboratories have attempted to generate LOX-1 inhibitors focusing mainly on substrate mimics or natural products. Falconi et al[17] used modified phospholipids that bind to the tunnel in the LOX-1 molecule, and observed that their compounds prevented the uptake ox-LDL, but only at high concentrations. Sawamura and coworkers[20] identified inhibitors from food extracts and found that procyanidins inhibited ox-LDL uptake in CHO cells expressing LOX-1; these compounds also prevented the uptake of ox-LDL, but only at high concentrations. Yoshiizumi et al[18] reported on the inhibitory properties of sulfatid derivatives on scavenger receptors and observed that 2,4-bis(octadecanoylamino) benzenesulfonic acid prevented LDL from binding to macrophages. Using cell-based binding assays and molecular docking simulations, Biocca et al[21] recently showed that statins bind the hydrophobic tunnel and can inhibit ox-LDL binding to LOX-1, again in high concentrations. Similarly, aspirin also been reported to reduce ox-LDL mediated LOX-1 expression[34]. However, these studies do not show any direct interaction of aspirin with the LOX-1 receptor.

In summary, LOX-1 is a promising novel target of therapy of atherosclerosis and related disorders. Through virtual screening technique, several potential inhibitors of LOX-1 have been identified, and two of these Mol-4 and Mol-5, were found to bind strongly with the LOX-1 protein. Cell based assays indicate that these molecules inhibit the uptake of ox-LDL and reduce downstream effects like MAPK activation. Interestingly, these compounds were found to significantly reduce the expression of adhesion molecules on endothelial cells and subsequent monocyte adhesion. We will be evaluating the pharmacokinetics (absorption, distribution, metabolism, and excretion) of these agents in near future.

Methods for Examples 1-8

Virtual Screening to Identify Potential Small-Molecule Inhibitors:

In order to locate LOX-1 inhibitors, we screened two subsets of the of the ZINC data base[23]. The compounds in this data base obey the Lipinski rule, a rule of thumb for a compound to be orally active as a drug[35]. We carried out the search on two subsets namely, 'clean leads' and 'clean drug-like' that contain chemical data on 5,735,035 and 13,195,609 small molecules respectively. The notation "clean" indicates that the compounds in the subset do not contain aldehydes, thiols, or Michael acceptor sites. These compounds are prone to have toxicity issues[36]. The virtual screening procedures were carried out using the software package SYBYL[24]. In preparation for the docking calculations, the geometry of the protein molecule (PDB code 1YPQ) was optimized using energy minimization techniques after the addition of hydrogen atoms. The ZINC datasets were reformatted to Sybyl Line Notation (SLN) compatible with the software package SYBYL. The next step was the assignment of the binding pocket and it was done using the SiteID module in SYBYL, which identifies potential binding sites within the protein molecule[37]. The largest cavity obtained from this calculation was in agreement with the ligand binding site observed in the crystal structure 12 and also with the conclusions of the modeling studies of LOX-1 with oxidized phospholipid 16.

Following the binding site identification, a MOLCAD surface was generated to incorporate all amino acids present on the binding surface within 5 Å. Additionally we identified a few potential hydrogen bond donors and acceptors in the active site as a part of the pharmacophore preparation. We performed the virtual screening using UNITY search module in SYBYL to identify molecules that could have the potential hydrogen bonding interactions and are capable to fit inside the MOLCAD surface generated in the binding pocket. This step served as a filter to generate a small subset of molecules that has potential to bind to LOX-1.

Scoring Functions and the Estimating the Probability of Binding:

The molecules belonging to the subset were docked to the binding site of LOX-1 using Suflex Dock-Gemox module SYBYL using default parameters. This procedure generates a protocol which is an idealized representation of the binding site that simulates the binding environment experienced by the ligand. The use of protomol expedites the docking process[38]. The docking analysis lists the C-Scores (consolidated scores) for the each molecule which is a measure of the goodness of fit. The C-Score function combines the binding score obtained from five different scoring algorithms namely, FlexX(Total Score), G_Score, PMF_Score, D_Score and ChemScore. These scores account for various interactions such as hydrogen bonding, electrostatic and hydrophobic interactions, entropy and solvation. C-Score 5 means that the binding score obtained from all five different scoring algorithms are above threshold and the ligand molecule has favorable interactions in the binding pocket[38]. While C score is a good indicator of binding, it is not a measure of the activity of the molecule. It should be pointed out that although all the molecules that we tested have a C score of 5, they do not have similar interactions at the binding pocket and each molecule has its unique mode of binding (FIG. 2B).

Protein Expression and Purification:

The C-terminal domain of LOX-1 was expressed by using the protocols reported earlier[12]. As this domain contains several disulfide bridges, it was co-expressed with DsbC, a Chaperone disulfide isomerase. The genes were custom synthesized by Genscript (Piscataway, N.J.) using gene map described in Park el al[12]. It encodes for 147 amino acids for the LOX-1 fragment (residues 136-273) and 236 amino acids for DsbC. The gene was incorporated into a pET15b vectors by Genscript. The vectors were then transformed into Dh5α cells for amplification and BL21 (DE3) *E. coli* (Novagen) cells for expression. The proteins were expressed by adding 0.4 mM isopropyl β-D-thiogalactoside in *E. coli* cells grown in LB medium containing kanamycin, tetracycline, and carbenicillin at 23° C., with 250 rpm agitation, for 20 h. The protein was purified using a nickel-nitrilotriacetic acid column (Qiagen, Valencia, Calif.). And then, the protein samples were concentrated to 10 mg/ml.

Thermal Shift Assay:

LOX-1 protein was incubated with fluorescent dye Sypro Orange (Invitrogen/Life Technologies, Grand Island, N.Y.) and the thermal unfolding of the LOX-1 protein was monitored by measuring the fluorescence using Bio-Rad Real Time PCR machine. We measured the melting temperatures in the absence and presence of the inhibitors 4 tM of LOX-1 protein was incubated with Sypro Orange and heated in stepwise increments of 0.5° C. per min from 25-99° C. The wavelength for excitation was set to 490 and emission was set to 575 nm for Sypro Orange. Fluorescence was measured after every minute for each 0.5° C. increase.

Culture of Human Umbilical Vein Endothelial Cells (HUVECs):

The primary HUVECs were purchased from ATCC (Manassas, Va.) and cultured in vascular cell basal medium with supplements (including 10 mL fetal bovine serum, 10 mM L-glutamine, 0.5 tg hydrocortisone hem isuccinate, 25 tg ascorbic acid, 2.5 ng rhVEGF, 2.5 ng rhEGF, 2.5 ng rh FGF, 7.5 ng rhIGF-1 and 0.375 units heparin sulfate). Cells from passages 3 and 4 were used in this study.

Dil-Ox-LDL Uptake Measurement:

HUVECs were plated into 6-well plates and cultured until the cells reached 70% confluence. The cells were exposed to 5 tg/mL Dil-ox-LDL for 30 min after treatment with 200 nM of each of 5 molecules for 30 min, and then washed with PBS for 3 times. After washing, the cells were digested with trypsin and washed with PBS, and suspended in 400 tL PBS, and analyzed with a flow-cytometer (Becton Dickinson, Mountain View, Calif.). For further confirm the inhibitory effects of Mol-5 on Dil-ox-LDL uptake, we also measured Dil-ox-LDL uptake by CHO cells after exposure to 0, 20, 200 and 200 nM Mol-5 for 30 min. The CHO cells were stably transfected with human LOX-1 cDNA.

Western Blotting:

HUVECs were plated into 6-well cell culture plates. When the cells were reached 70% confluence, they were treated with 200 nM of each of 5 molecules for 30 min, and subsequently exposed to 5 tg/mL ox-LDL for 6 h. After washing with PBS for 2 times, the cells were treated with Cell Lysis Buffer (Promega, Madison, Wis.) with protease Inhibitor and phosphatase Inhibitor (Sigma-Aldrich, St. Louis, Mo.). The protein concentrations were measured by Bradford protein assay. Proteins (20 tg) were separated by electrophoresis in 12% precast SDS-PAGE gels, and were transferred onto Nitrocellulose Blotting Membrane (GE Healthcare Life Science, Piscataway, N.J.). The membranes were then incubated with LOX-1, VCAM-1 (Abcam, Cambridge, Mass.), ERK1/2, phospho-ERK1/2, phospho-p38MAPK (Cell Signaling Technology, Inc., Danvers, Mass.), or 13-actin (Santa Cruz Biotechnology, Inc., Dallas, Tex.) primary antibodies (1:1000~1:2000) in blocking solution at 4° C. overnight. Following wash with TBS-1 for 3 times, the blots were incubated with HRP-conjugated secondary antibodies (1:10000) in blocking solution for 1 hour at room temperature. After 3 washes with PBS, the blots were treated with Western Blotting Luminol Reagents (Santa Cruz Biotechnology) for 3 min and then exposed to Blue Basic Autorad Film (GeneMate, Kaysville, Utah). The protein bands were scanned by a Gel Doc™ XR System (Bio-Rad, Hercules, Calif.), and the density of each band was quantified by Image J software. The relative expression of target proteins was calculated with comparison to 13-actin bands.

Real-Time Polymerase Chain Reaction (q-PCR):

HUVECs were plated into 12-well plates, and treated with 0, 20, 200 and 2000 nM of each of 5 molecules for 5 for 30 min, and subsequently exposed to 5 tg/mL ox-LDL for 6 h at 37° C. Total RNA was isolated from the treated HUVECs by using a RNeasy Mini-Kit (Invitrogen/Life Technologies) according to the manufacturer's instructions. Prior to using, RNA was treated with DNase I and diluted to 100 ng/tL. 100 ng RNA was applied to synthesize cDNA with SuperScript III 1st Strand DNA Synthesis Kit. qPCR was performed using the Applied Biosystems Fast 7500HT real-time PCR system with a 20 tL reaction volume including 10 tL GoTaq qPCR Master Mix (Promega, Madison, Wis.), 100 ng of cDNA and 0.3 tM primers. Data was analyzed by using MX3000P software. Relative mRNA expression was quantified using the comparative threshold cycle (Ct) method. The sequences of primers used for PCR reaction have been described previously[30].

Monocyte Adhesion Assay:

Human monocytes were isolated from blood from the healthy donors and cultured in DMEM supplemented with 10% FBS. HUVECs were plated into 6-well plates. When the cells reached 70-80% confluence, they were treated with 200 nM of each of 5 molecules for 30 min, and subsequently exposed to 5 tg/mL ox-LDL for 6 h. After washing with PBS, the medium was replaced, and then monocytes (5×105) were added to each well (4 wells/group) onto HUVECs. Thirty minutes later, the medium containing monocytes were aspired and the unattached monocytes were carefully washed out with PBS. Five fields of each well were randomly captured under a microscope. The number of adherent monocyte was counted and averaged.

of Mol-5, also known as 1-(3,5-dimethyl-1H-pyrazol-1-yl)-3-phenoxypropan-2-ol (DPP), such as affinity and bioavailability. Four sites on the molecule were selected for alterations. They are designated as $R^1$, $R^2$, $R^3$ and $R^4$ as depicted in Formula (II).

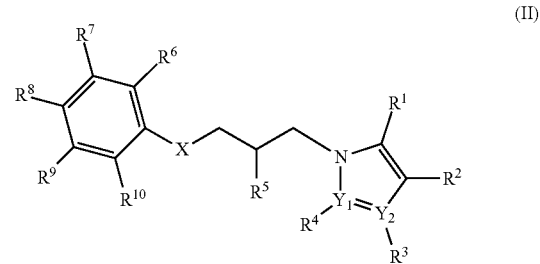

(II)

In silico analyses indicated that modified versions of DPP comprising the groups listed in Table 3 may bind well to LOX-1. These compounds may be synthesized and tested.

TABLE 3

| Compound | $R^1$ | $R^2$ | $R^3$ | $R^4$ | $R^5$ | $R^8$ | $R^{10}$ | $R^6, R^7, R^9$ | X | $Y_1, Y_2$ |
|---|---|---|---|---|---|---|---|---|---|---|
| Zinc00261354 | —$CH_3$ | —H | —$CH_3$ | absent | —OH | —H | —H | —H | —O— | N, C |
| 1. | —$CH_2CH_3$ | —H | —$CH_3$ | absent | —OH | —H | —H | —H | —O— | N, C |
| 2. | —$CH_2CH_2CH_3$ | —H | —$CH_3$ | absent | —OH | —H | —H | —H | —O— | N, C |
| 3. | —$NH_2$ | —H | —$CH_3$ | absent | —OH | —H | —H | —H | —O— | N, C |
| 4. | —$CH_2NH_2$ | —H | —$CH_3$ | absent | —OH | —H | —H | —H | —O— | N, C |
| 5. | —$CH_2$ | —H | —$CH_2CH_3$ | absent | —OH | —H | —H | —H | —O— | N, C |
| 6. | —$CH_3$ | —H | —$CH_2CH_2CH_3$ | absent | —OH | —H | —H | —H | —O— | N, C |
| 7. | —$CH_2CH_3$ | —H | —$CH_2CH_3$ | absent | —OH | —H | —H | —H | —O— | N, C |
| 8. | —$CH_3$ | —$CH_3$ | —$CH_3$ | absent | —OH | —H | —H | —H | —O— | N, C |
| 9. | —$CH_2CH_3$ | —$CH_2CH_3$ | —$CH_2CH_3$ | absent | —OH | —H | —H | —H | —O— | N, C |
| 10. | —$CH_3$ | —H | —$CH_3$ | absent | —OH | —Cl | —Cl | —H | —O— | N, C |
| 11. (M5_1) | —$CH_3$ | —H | —Cl | absent | —OH | —H | —H | —H | —O— | N, C |
| 12. (M5_4) | —$CH_3$ | —H | —CN | absent | —OH | —H | —H | —H | —O— | N, C |
| 13. (M5_2) | —H | —H | absent | —I | —OH | —H | —H | —H | —O— | C, N |
| 14. (M5_3) | —H | —H | absent | —H | —OH | —H | —H | —H | —O— | C, N |
| 15. (M5_5) | —H | —H | absent | —$CH_3$ | —OH | —H | —H | —H | —O— | C, N |
| 16. (M5_6) | —H | —$CH_3$ | absent | —$CH_2CH_3$ | —OH | —H | —H | —H | —O— | C, N |

Cytotoxicity Assay:

HUVECs (1×10³/well) were plated into 96-well plates and cultured overnight. The medium was replaced after an overnight culture, and the cells were subsequently incubated with 20, 200 and 2000 nM of each candidate molecules (Mol-1, Mol-2, Mol-3, Mol-4, and Mol-5 diluted in ultrapure water) for 6.5 h. As control, cells were incubated with the same aliquots of ultrapure water. Cytotoxicity was tested using a Pierce LDH Cytotoxicity Assay Kit (Invitrogen/Life Technologies) as per manufacturer's instructions. The LDH cytotoxicity was measured by absorbance of A490 minus A680.

Statistical Analysis:

Statistical analysis was performed with SPSS 16.0 software. Data are presented as means and standard deviation (SD). Univariate comparisons of means were evaluated using one-way ANOVA with Tukey's post-hoc adjustment for multiple comparisons. A P value<0.05 was considered significant.

Example 9. Chemical Modifications of Mol-5

Figure 7A:
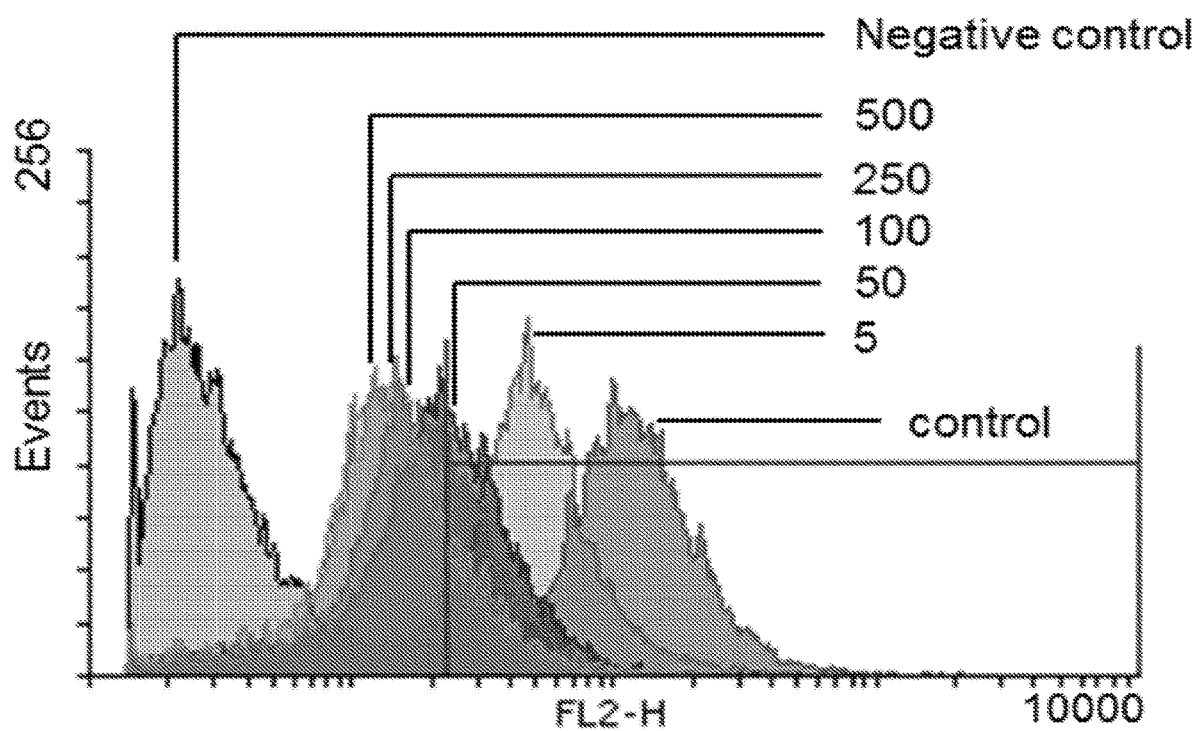
FIG. 7A depicts flow cytometry measurements using human primary aortic endothelial cells in the presence of 0, 5, 50 100, 250 and 500 nm of Formula XVI.
Figure 7B:
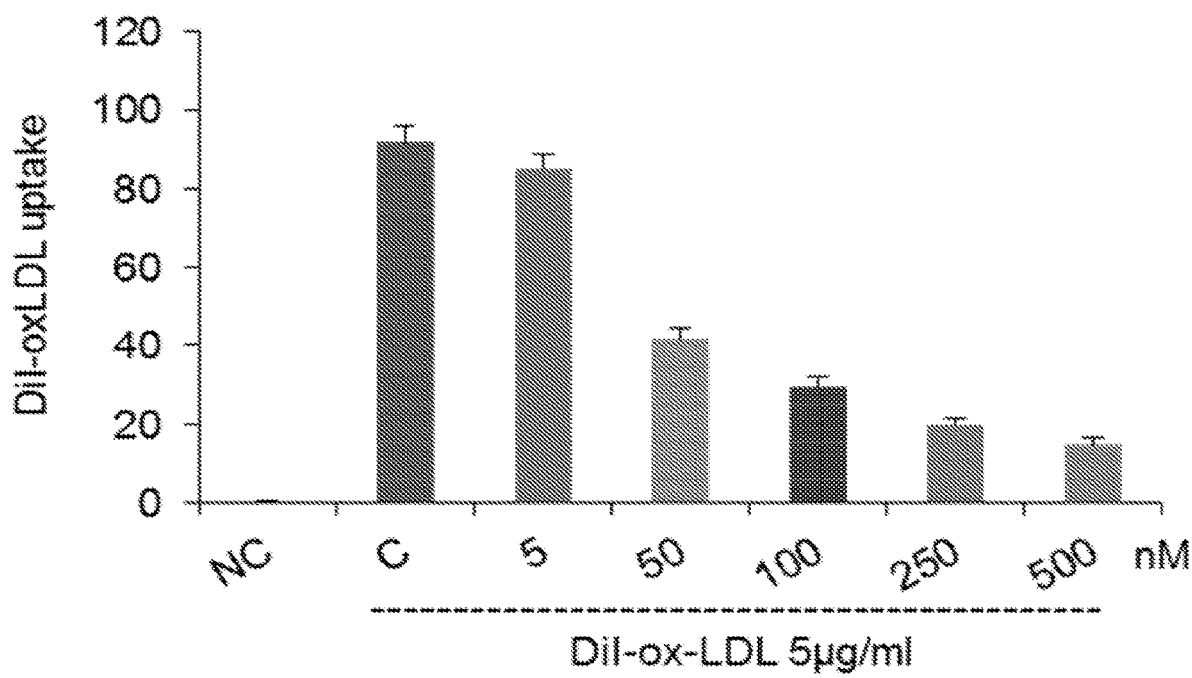
FIG. 7B depicts the percentage of internalized ox-LDL. The x-axis represents Formula XVI concentration (nM) and the y-axis represents ox-LDL uptake by ECs.
Figure 7C:
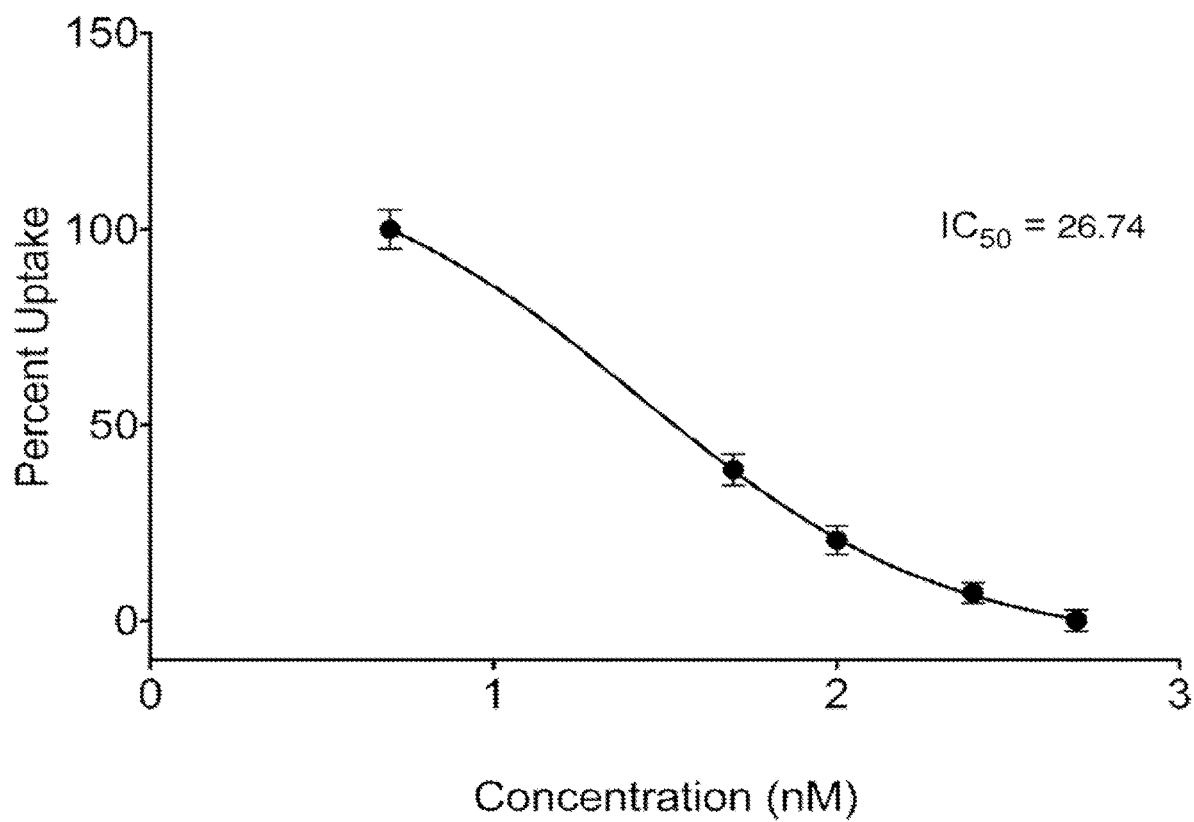
FIG. 7C depicts a plot showing that Formula XVI reduced ox-LDL uptake in a dose dependent manner, with an $IC_{50}$ value of 26.74 nM.

Several chemical modifications of this compound were considered which could enhance the therapeutic properties Example 10. Effect of the Compound of Formula XVI on Ox-LDL Uptake by HUVECs Ox-LDL uptake by human primary aortic endothelial cells was measured after exposure to 0, 5, 50, 100, 250 and 500 nM of the compound of Formula XVI (compound 13 in Table 3) using flow cytometry. As shown in FIG. 7A and FIG. 7B, Formula XVI reduced ox-LDL uptake in a dose dependent manner, with an $IC_{50}$ value of 26.74 nM (FIG. 7C).

REFERENCES FOR THE EXAMPLES

1. Lu, J., Mitra, S., Wang, X., Khaidakov, M., & Mehta, J. L. Oxidative stress and lectin-like ox-LDL-receptor LOX-1 in atherogenesis and tumorigenesis. *Antioxid. Redox. Signal.* 15, 2301-2333 (2011).
2. Mehta, J. L. & Li, D. Y. Identification and autoregulation of receptor for OX-LDL in cultured human coronary artery endothelial cells. *Biochem Biophys. Res Commun* 248, 511-514 (1998).
3. Mehta, J. L. et al. Deletion of LOX-1 reduces atherogenesis in LDLR knockout mice fed high cholesterol diet. *Circ. Res.* 100, 1634-1642 (2007).

4. Wang, X., Phillips, M. I., & Mehta, J. L. LOX-1 and angiotensin receptors, and their interplay. *Cardiovasc Drugs Ther* 25, 401-417 (2011).
5. Li, D. et al. LOX-1 inhibition in myocardial ischemia-reperfusion injury: modulation of MMP-1 and inflammation. *Am. J. Physiol Heart Circ. Physiol* 283, H1795-H1801 (2002).
6. Kataoka, K. et al. LOX-1 pathway affects the extent of myocardial ischemia-reperfusion injury. *Biochem Biophys. Res Commun* 300, 656-660 (2003).
7. Wang, X. et al. Lectin-like oxidized low-density lipoprotein receptor-1 (LOX-1) and cardiac fibroblast growth. *Hypertension* 60, 1437-1442 (2012).
8. Dandapat, A., Hu, C., Sun, L., & Mehta, J. L. Small concentrations of oxLDL induce capillary tube formation from endothelial cells via LOX-1-dependent redox-sensitive pathway. *Arterioscler. Thromb. Vasc. Biol.* 27, 2435-2442 (2007).
9. Mehta, J. L. et al. LOX-1: a new target for therapy for cardiovascular diseases. *Cardiovasc. Drugs Ther.* 25, 495-500 (2011).
10. Chen, M., Narumiya, S., Masaki, T., & Sawamura, T. Conserved C-terminal residues within the lectin-like domain of LOX-1 are essential for oxidized low-density-lipoprotein binding. *Biochem. J.* 355, 289-296 (2001).
11. Xie, Q. et al. Human lectin-like oxidized low-density lipoprotein receptor-1 functions as a dimer in living cells. *DNA Cell Biol.* 23, 111-117 (2004).
12. Park, H., Adsit, F. G., & Boyington, J. C. The 1.4 angstrom crystal structure of the human oxidized low density lipoprotein receptor lox-1. *J. Biol. Chem.* 280, 13593-13599 (2005).
13. Ohki, I. et al. Crystal structure of human lectin-like, oxidized low-density lipoprotein receptor 1 ligand binding domain and its ligand recognition mode to OxLDL. *Structure.* 13, 905917 (2005).
14. Segrest, J. P., Jones, M. K., De, L. H., & Dashti, N. Structure of apolipoprotein B-100 in low density lipoproteins. *J Lipid Res* 42, 1346-1367 (2001).
15. S. Tate Structure and mode of ligand recognition of the oxidized LDL receptor, LOX-1. in *Functional and Structural Biology on the Lipo-network, Transworld Research Network* (ed. K. Morikawa and S. Tate) 179-198 (2006).
16. Francone, O. L. et al. The hydrophobic tunnel present in LOX-1 is essential for oxidized LDL recognition and binding. *J. Lipid Res.* 50, 546-555 (2009).
17. Falconi, M. et al. Design of a novel LOX-1 receptor antagonist mimicking the natural substrate. *Biochem Biophys. Res Commun* 438, 340-345 (2013).
18. Yoshiizumi, K., Nakajima, F., Dobashi, R., Nishimura, N., & Ikeda, S. Studies on scavenger receptor inhibitors. Part 1: synthesis and structure-activity relationships of novel derivatives of sulfatides. *Bioorg. Med Chem.* 10, 2445-2460 (2002).
19. Yoshiizumi, K., Nakajima, F., Dobashi, R., Nishimura, N., & Ikeda, S. 2,4-Bis(octadecanoylamino)benzenesulfonic acid sodium salt as a novel scavenger receptor inhibitor with low molecular weight. *Bioorg. Med Chem. Lett.* 14, 2791-2795 (2004).
20. Nishizuka, T. et al. Procyanidins are potent inhibitors of LOX-1: a new player in the French Paradox. *Proc Jpn. Acad Ser. B Phys Biol Sci* 87, 104-113 (2011).
21. Biocca, S. et al. Molecular mechanism of statin-mediated LOX-1 inhibition. *Cell Cycle* 14, 1583-1595 (2015).
22. Kostner, G. M. et al. HMG CoA reductase inhibitors lower LDL cholesterol without reducing Lp(a) levels. *Circulation* 80, 1313-1319 (1989).
23. Irwin, J. J., Sterling, T., Mysinger, M. M., Bolstad, E. S., & Coleman, R. G. ZINC: A Free Tool to Discover Chemistry for Biology. *J. Chem Inf Model* 52, 1757-1768 (2012).
24. SYBYL-X 2.0. Tripos International, 1699 South Hanley Rd., St. Louis, Mo., 63144, USA. Tripos International, 1699 South Hanley Rd., St. Louis, Mo., 63144, USA. 2012.
25. Niesen, F. H., Berglund, H., & Vedadi, M. The use of differential scanning fluorimetry to detect ligand interactions that promote protein stability. *Nat. Protoc.* 2, 2212-2221 (2007).
26. Sakamoto, N. et al. Role of LOX-1 in monocyte adhesion-triggered redox, Akt/eNOS and Ca2+ signaling pathways in endothelial cells. *J Cell Physiol* 220, 706-715 (2009).
27. Ding, Z. et al. Concentration polarization of ox-LDL activates autophagy and apoptosis via regulating LOX-1 expression. *Sci Rep* 3, 2091 (2013).
29. Libby, P. Inflammation in atherosclerosis. *Arterioscler. Thromb. Vasc. Biol.* 32, 2045-2051 (2012).
30. Libby, P. Inflammation in atherosclerosis. *Nature* 420, 868-874 (2002).
31. Khaidakov, M. et al. Large Impact of Low Concentration Oxidized LDL on Angiogenic Potential of Human Endothelial Cells: A Microarray Study. *PLoS. ONE.* 7, e47421 (2012).
32. Silvestre, H. L., Blundell, T. L., Abell, C., & Ciulli, A. Integrated biophysical approach to fragment screening and validation for fragment-based lead discovery. *Proc Natl Acad Sci USA* 110, 12984-12989 (2013).
33. Iwamoto, S. et al. Generation and characterization of chicken monoclonal antibodies against human LOX-1. *MAbs.* 1, 357-363 (2009).
34. Sethu, S. et al. Immunogenicity to biologics: mechanisms, prediction and reduction. *Arch Immunol Ther Exp (Warsz.)* 60, 331-344 (2012).
35. Mehta, J. L., Chen, J., Yu, F., & Li, D. Y. Aspirin inhibits ox-LDL-mediated LOX-1 expression and metalloproteinase-1 in human coronary endothelial cells. *Cardiovasc Res* 64, 243-249 (2004).
36. Lipinski, C. A., Lombardo, F., Dominy, B. W., & Feeney, P. J. Experimental and computational approaches to estimate solubility and permeability in drug discovery and development settings. *Adv Drug Deliv. Rev* 46, 3-26 (2001).
37. Smith, G. F. Designing drugs to avoid toxicity. *Prog Med Chem.* 50, 1-47 (2011).
38. Sekhar, P. N. et al. In silico modeling and hydrogen peroxide binding study of rice catalase. *In Silico. Biol* 6, 435-447 (2006).
39. Jain, A. N. Surflex-Dock 2.1: robust performance from ligand energetic modeling, ring flexibility, and knowledge-based search. *J Comput Aided Mol Des* 21, 281-306 (2007).

What is claimed is:

1. A method of inhibiting oxidized low-density lipoprotein receptor 1 (LOX-1) in a cell, the method comprising contacting the cell with an effective amount of a compound having a structure represented by a formula:

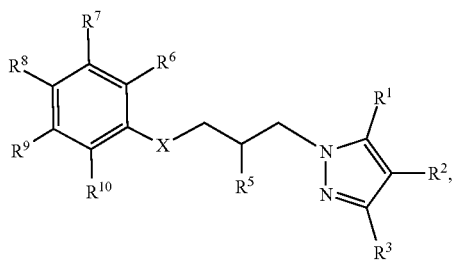

wherein:
X is selected from the group consisting of oxygen, sulfur, sulfoxide, sulfone, and NH;
$R^1$ is selected from the group consisting of hydrogen, hydroxyl, aldehyde, haloformyl, hydroperoxyl, alkyl, alkenyl, alkynyl, aryl, halogen, aminoalkyl, amino, phosphoro, sulfhydryl, sulfino, sulfo, and cyano;
$R^2$ is selected from the group consisting of hydrogen, hydroxyl, aldehyde, haloformyl, hydroperoxyl, alkyl, alkenyl, alkynyl, unsubstituted aryl, halogen, aminoalkyl, amino, phosphoro, sulfhydryl, sulfino, sulfo, and cyano;
$R^3$ is selected from the group consisting of hydrogen, hydroxyl, aldehyde, haloformyl, hydroperoxyl, alkyl, alkenyl, alkynyl, aryl, halogen, aminoalkyl, amino, phosphoro, sulfhydryl, sulfino, sulfo, and cyano;
$R^5$ is hydroxyl; and
each of $R^6$, $R^7$, $R^8$, $R^9$, and $R^{10}$ is independently selected from the group consisting of hydrogen, hydroxyl, aldehyde, haloformyl, hydroperoxyl, alkyl, alkenyl, alkynyl, aryl, halogen, phosphoro, sulfhydryl, sulfino, sulfo, and cyano, thereby inhibiting oxidized LOX-1.

2. The method of claim 1, wherein X is oxygen.
3. The method of claim 1, wherein $R^1$ is selected from the group consisting of hydrogen, amino, and C1-C5 alkyl.
4. The method of claim 1, wherein $R^2$ is selected from the group consisting of hydrogen and C1-C5 alkyl.
5. The method of claim 1, wherein $R^3$ is selected from the group consisting of hydrogen, C1-C5 alkyl, cyano, and halogen.
6. A method of inhibiting oxidized low-density lipoprotein receptor 1 (LOX-1) in a cell, the method comprising contacting the cell with an effective amount of a compound selected from:

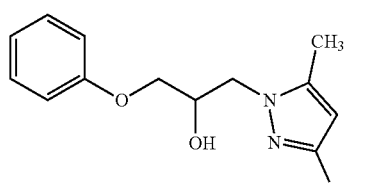

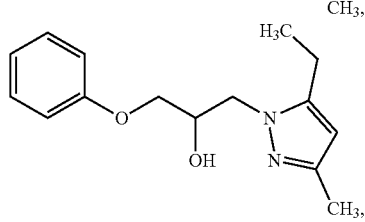

-continued

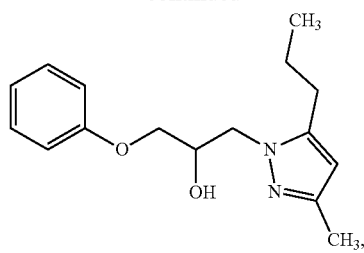

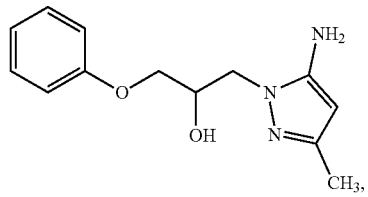

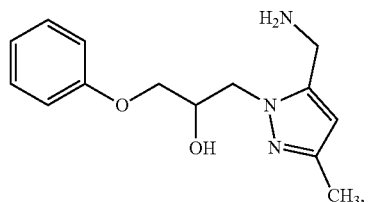

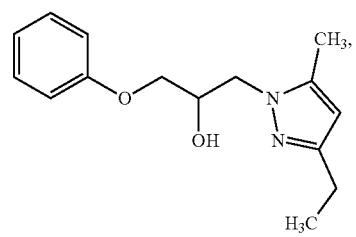

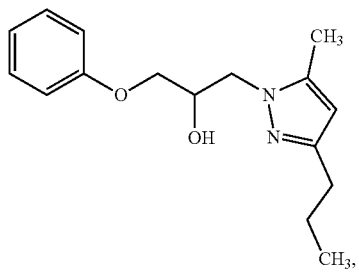

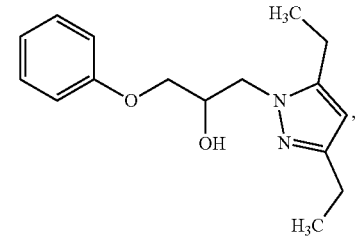

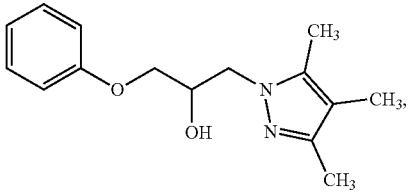

-continued

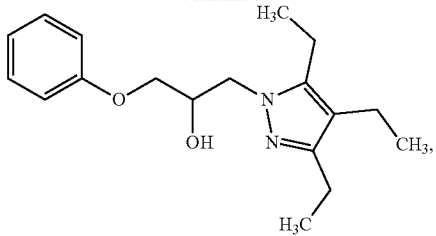

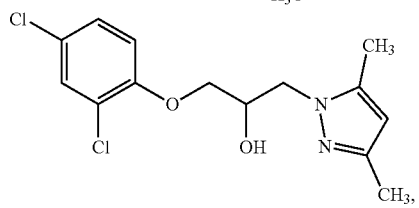

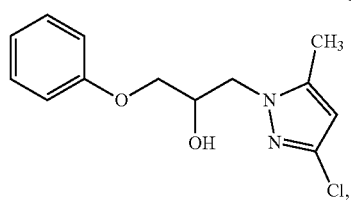

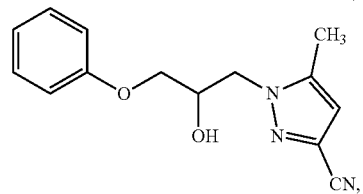

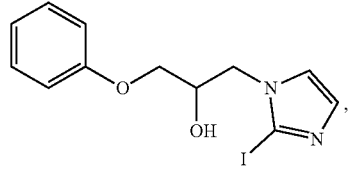

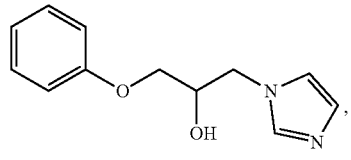

-continued

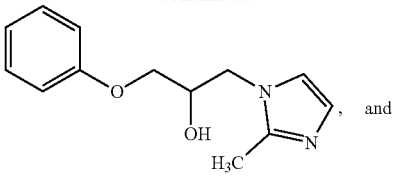, and

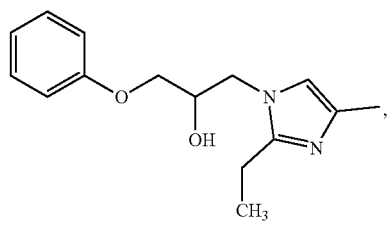

thereby inhibiting oxidized LOX-1.

7. The method of claim 1, wherein the compound is:

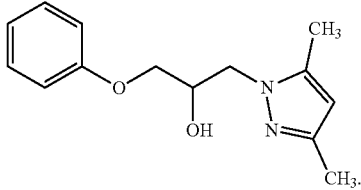 [SMILES: Cc1cc(C)n(CC(O)COc2ccccc2)n1]

8. The method of claim 1, wherein the cell is human.

9. The method of claim 1, wherein the cell has been isolated from a subject prior to the administering step.

10. The method of claim 1, wherein contacting is via administration to a subject.

11. The method of claim 10, wherein the subject has been diagnosed with a need for treatment of a disorder associated with LOX-1 activity or elevated levels of ox-LDL.

\* \* \* \* \*